US012354186B2

(12) United States Patent
Jogan et al.

(10) Patent No.: US 12,354,186 B2
(45) Date of Patent: Jul. 8, 2025

(54) CUSTOMIZATION OF OVERLAID DATA AND CONFIGURATION

(71) Applicant: Cilag GmbH International, Zug (CH)

(72) Inventors: Matjaz Jogan, Philadelphia, PA (US); Zhifan F. Huang, Mason, OH (US); Shaun B. Schaeffer, Cincinnati, OH (US); Tyler N. Brehm, Cincinnati, OH (US); John E. Brady, Cincinnati, OH (US); Frederick E. Shelton, IV, Hillsboro, OH (US); Demetrius N. Harris, Austin, TX (US); Ellen E. Burkart, Liberty Township, OH (US); Madison K. Vanosdoll, Cincinnati, OH (US); Christopher Q. Seow, Cincinnati, OH (US); Cory G. Kimball, Hamilton, OH (US); Monica L. Z. Rivard, Cincinnati, OH (US); Leonardo N. Rossoni, Rahway, NJ (US); Matthew D. Cowperthwait, Cincinnati, OH (US); Risto Kojcev, Santa Clara, CA (US); Felix J. Bork, Schnürpflingen (DE)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/688,638

(22) Filed: Mar. 7, 2022

(65) Prior Publication Data
US 2022/0334787 A1 Oct. 20, 2022

Related U.S. Application Data

(60) Provisional application No. 63/284,326, filed on Nov. 30, 2021, provisional application No. 63/174,674, filed on Apr. 14, 2021.

(51) Int. Cl.
*G06T 11/00* (2006.01)
*A61B 34/00* (2016.01)
(Continued)

(52) U.S. Cl.
CPC .............. *G06T 11/00* (2013.01); *A61B 34/20* (2016.02); *A61B 34/25* (2016.02); *A61B 34/30* (2016.02);
(Continued)

(58) Field of Classification Search
CPC ..... G06T 11/00; G06T 2210/41; G06T 11/60; G06T 7/70; G06T 2200/24; A61B 34/20;
(Continued)

(56) References Cited

U.S. PATENT DOCUMENTS 4,171,700 A   10/1979   Farin
4,849,752 A   7/1989   Bryant
(Continued)

FOREIGN PATENT DOCUMENTS

EP   0408160 A1   1/1991
EP   0473987 A1   3/1992
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Ryan R Yang
(74) *Attorney, Agent, or Firm* — Condo Roccia Koptiw LLP

(57) ABSTRACT

A method of distributing data among members of a surgical team may include receiving imaging data, by a modular control tower, from a plurality of imaging devices, receiving device-dependent data, by the modular control tower, from
(Continued)

each of a plurality of intelligent surgical instruments, associating, by the modular control tower, a display device with a member of the surgical team, defining, by the modular control tower, a functional role for the member of the surgical team, and displaying, by the modular control tower, a augmented reality display by the display device. The augmented reality display on the display device may include virtual objects based on the imaging data, the device-dependent data, the functional role of the member of the surgical team, and a surgical activity by the member of the surgical team. An interactive surgical system may implement this method.

20 Claims, 23 Drawing Sheets

(51) Int. Cl.
| | |
|---|---|
| A61B 34/20 | (2016.01) |
| A61B 34/30 | (2016.01) |
| A61B 34/32 | (2016.01) |
| A61B 90/00 | (2016.01) |
| G06F 3/14 | (2006.01) |
| G06F 3/147 | (2006.01) |
| G06T 7/00 | (2017.01) |
| G06T 7/20 | (2017.01) |
| G06T 19/00 | (2011.01) |
| G06V 20/20 | (2022.01) |
| G08B 21/18 | (2006.01) |
| G16H 20/40 | (2018.01) |
| G16H 40/67 | (2018.01) |
| H04L 9/40 | (2022.01) |
| H04L 67/12 | (2022.01) |
| H04W 24/10 | (2009.01) |
| H04W 76/14 | (2018.01) |
| A61B 34/10 | (2016.01) |

(52) U.S. Cl.
CPC ............ *A61B 34/32* (2016.02); *A61B 34/76* (2016.02); *A61B 90/36* (2016.02); *A61B 90/361* (2016.02); *A61B 90/37* (2016.02); *A61B 90/39* (2016.02); *G06F 3/14* (2013.01); *G06F 3/1454* (2013.01); *G06F 3/147* (2013.01); *G06T 7/0012* (2013.01); *G06T 7/20* (2013.01); *G06T 19/006* (2013.01); *G06V 20/20* (2022.01); *G08B 21/182* (2013.01); *G16H 20/40* (2018.01); *G16H 40/67* (2018.01); *H04L 63/105* (2013.01); *H04L 67/12* (2013.01); *H04W 24/10* (2013.01); *H04W 76/14* (2018.02); *A61B 2034/102* (2016.02); *A61B 2034/2055* (2016.02); *A61B 2034/2072* (2016.02); *A61B 2090/365* (2016.02); *A61B 2090/368* (2016.02); *A61B 2090/371* (2016.02); *A61B 2090/372* (2016.02); *A61B 2090/373* (2016.02); *A61B 2090/3937* (2016.02); *A61B 2090/3975* (2016.02); *G06T 2207/10028* (2013.01); *G06T 2207/30024* (2013.01); *G06T 2210/41* (2013.01)

(58) Field of Classification Search
CPC ......... A61B 34/25; A61B 34/30; A61B 34/32; A61B 34/76; A61B 90/36; A61B 90/361; A61B 90/37; A61B 90/39; A61B 2034/102; A61B 2034/2055; A61B 2034/2072; A61B 2090/365; A61B 2090/368; A61B 2090/371; A61B 2090/372; A61B 2090/373; A61B 2090/3937; A61B 2090/3975; A61B 2207/10028; A61B 2207/30024; A61B 17/07292; A61B 90/98; A61B 17/1155; A61B 90/30; A61B 90/94; A61B 2017/00017; A61B 2017/00026; A61B 2017/00084; A61B 2017/00106; A61B 2017/00119; A61B 2017/00128; A61B 2017/00207; A61B 2017/00216; A61B 2017/00809; A61B 2017/00818; A61B 2017/07214; A61B 2017/07271; A61B 2017/1132; A61B 2017/4216; A61B 2018/00898; A61B 2034/2048; A61B 2034/2065; A61B 2034/254; A61B 2034/258; A61B 2090/064; A61B 2090/0807; A61B 2217/005; A61B 2217/007; A61B 17/07207; A61B 34/37; A61B 2017/00115; A61B 2017/00203; A61B 2090/502; G06F 3/14; G06F 3/011; G16H 40/67; G16H 30/40; G16H 40/60; G16H 40/63; G16H 40/20; G16H 50/20; G16H 50/70; G16H 70/20; G16H 30/20; H04L 63/105; H04L 67/12; H04L 67/131; H04L 69/40; H04W 24/10; H04W 76/14; H04W 84/18; H04W 12/06; H04W 12/50; G06V 10/764; G06V 40/20; G06V 2201/034; G06V 2201/03; G09G 2380/08
See application file for complete search history.

(56) References Cited

U.S. PATENT DOCUMENTS

| | | |
|---|---|---|
| D303,787 S | 10/1989 | Messenger et al. |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| 5,325,270 A | 6/1994 | Wenger et al. |
| 5,425,375 A | 6/1995 | Chin et al. |
| D379,346 S | 5/1997 | Mieki |
| 5,690,504 A | 11/1997 | Scanlan et al. |
| 5,693,042 A | 12/1997 | Boiarski et al. |
| 5,724,468 A | 3/1998 | Leone et al. |
| 6,049,467 A | 4/2000 | Tamarkin et al. |
| 6,055,458 A | 4/2000 | Cochran et al. |
| D431,811 S | 10/2000 | Nishio et al. |
| 6,179,136 B1 | 1/2001 | Kluge et al. |
| 6,269,411 B1 | 7/2001 | Reasoner |
| 6,288,606 B1 | 9/2001 | Ekman et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,843,657 B2 | 1/2005 | Driscoll et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,331,699 B2 | 2/2008 | Gawalkiewicz et al. |
| 7,344,532 B2 | 3/2008 | Goble et al. |
| 7,353,068 B2 | 4/2008 | Tanaka et al. |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |

(56) References Cited

U.S. PATENT DOCUMENTS

| | | |
|---|---|---|
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| 8,086,008 B2 | 12/2011 | Coste-Maniere et al. |
| D655,678 S | 3/2012 | Kobayashi et al. |
| D657,368 S | 4/2012 | Magee et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,968,296 B2 | 3/2015 | McPherson |
| 8,986,288 B2 | 3/2015 | Konishi |
| 9,017,326 B2 | 4/2015 | Dinardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,427,255 B2 | 8/2016 | Griffith et al. |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| 9,867,670 B2 | 1/2018 | Brannan et al. |
| 9,892,564 B1 | 2/2018 | Cvetko et al. |
| 9,907,196 B2 | 2/2018 | Susini et al. |
| 9,935,794 B2 | 4/2018 | Cao et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,019 B2 | 1/2019 | Nawana et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,610,310 B2 | 4/2020 | Todd et al. |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| 11,006,100 B1 | 5/2021 | Douglas |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,114,199 B2 * | 9/2021 | Moctezuma de la Barrera ......... H04N 23/00 |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |

(56) References Cited

U.S. PATENT DOCUMENTS

| | | |
|---|---|---|
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,471,206 B2 | 10/2022 | Henderson et al. |
| 11,478,820 B2 | 10/2022 | Bales et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| 2001/0029315 A1 | 10/2001 | Sakurai et al. |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0076363 A1 | 4/2007 | Liang et al. |
| 2007/0211930 A1 | 9/2007 | Dolwick et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0131929 A1 | 5/2009 | Shimizu |
| 2009/0192524 A1 | 7/2009 | Itkowitz et al. |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0125149 A1 | 5/2011 | El-Galley et al. |
| 2011/0130689 A1 | 6/2011 | Cohen et al. |
| 2011/0190588 A1 | 8/2011 | Mckay |
| 2011/0245630 A1 | 10/2011 | St. Pierre et al. |
| 2011/0273465 A1 | 11/2011 | Konishi et al. |
| 2011/0298814 A1 | 12/2011 | Mathew et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2013/0031201 A1 | 1/2013 | Kagan et al. |
| 2013/0038707 A1 | 2/2013 | Cunningham et al. |
| 2013/0176220 A1 | 7/2013 | Merschon et al. |
| 2013/0197357 A1 | 8/2013 | Green et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2013/0303851 A1 | 11/2013 | Griffith et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2015/0019259 A1 | 1/2015 | Qureshi et al. |
| 2015/0070388 A1 | 3/2015 | Sheaffer et al. |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2016/0045247 A1 | 2/2016 | Heim et al. |
| 2016/0058286 A1 | 3/2016 | Joshua et al. |
| 2016/0066184 A1 | 3/2016 | Bhargav-Spantzel et al. |
| 2016/0074096 A1 | 3/2016 | Lieu |
| 2016/0120591 A1 | 5/2016 | Smith et al. |
| 2016/0225192 A1 | 8/2016 | Jones et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0090507 A1 | 3/2017 | Wiener et al. |
| 2017/0189096 A1 | 7/2017 | Danziger et al. |
| 2017/0202595 A1 | 7/2017 | Shelton, IV |
| 2017/0251305 A1 | 8/2017 | Fathollahi |
| 2017/0252091 A1 | 9/2017 | Honda |
| 2017/0258526 A1 | 9/2017 | Lang |
| 2017/0296213 A1 | 10/2017 | Swensgard et al. |
| 2017/0319259 A1 | 11/2017 | Dunning |
| 2017/0333275 A1 | 11/2017 | Itkowitz et al. |
| 2017/0360466 A1 | 12/2017 | Brown et al. |
| 2018/0014872 A1 | 1/2018 | Dickerson |
| 2018/0032130 A1 | 2/2018 | Meglan |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0173323 A1 | 6/2018 | Harvey et al. |
| 2018/0221005 A1 | 8/2018 | Hamel et al. |
| 2018/0228528 A1 | 8/2018 | Fraasch et al. |
| 2018/0243573 A1 | 8/2018 | Yoder et al. |
| 2018/0262916 A1 | 9/2018 | Polley et al. |
| 2018/0263557 A1 | 9/2018 | Kahlman |
| 2018/0289338 A1 | 10/2018 | Meador et al. |
| 2018/0317826 A1 | 11/2018 | Muhsin et al. |
| 2018/0333207 A1 | 11/2018 | Moctezuma De La Barrera |
| 2018/0368930 A1 | 12/2018 | Esterberg et al. |
| 2019/0035153 A1 | 1/2019 | Dange |
| 2019/0038362 A1 | 2/2019 | Nash et al. |
| 2019/0069957 A1 | 3/2019 | Barral et al. |
| 2019/0104919 A1 | 4/2019 | Shelton, IV et al. |
| 2019/0125361 A1 | 5/2019 | Shelton, IV et al. |
| 2019/0125451 A1 | 5/2019 | Srimohanarajah et al. |
| 2019/0125454 A1 | 5/2019 | Stokes et al. |
| 2019/0125455 A1 | 5/2019 | Shelton, IV et al. |
| 2019/0125459 A1 | 5/2019 | Shelton et al. |
| 2019/0183576 A1 | 6/2019 | Fahim et al. |
| 2019/0183591 A1 | 6/2019 | Johnson et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201046 A1 | 7/2019 | Shelton, IV et al. |
| 2019/0201102 A1 | 7/2019 | Shelton, IV et al. |
| 2019/0201116 A1 | 7/2019 | Shelton, IV et al. |
| 2019/0201127 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0205001 A1 | 7/2019 | Messerly et al. |
| 2019/0206004 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206565 A1 | 7/2019 | Shelton, IV |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |

(56) References Cited

U.S. PATENT DOCUMENTS

| | | |
|---|---|---|
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015895 A1 | 1/2020 | Frielinghaus et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015902 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015924 A1 | 1/2020 | Scheib et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0093357 A1 | 3/2020 | Scott et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0159313 A1 | 5/2020 | Gibby et al. |
| 2020/0237031 A1 | 7/2020 | Daniels et al. |
| 2020/0237452 A1 | 7/2020 | Wolf et al. |
| 2020/0268469 A1 | 8/2020 | Wolf et al. |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0322516 A1 | 10/2020 | Doser et al. |
| 2020/0342228 A1 | 10/2020 | Prevrhal et al. |
| 2020/0359892 A1 | 11/2020 | Rollins et al. |
| 2020/0384287 A1 | 12/2020 | Hetz |
| 2020/0405529 A1 | 12/2020 | Taylor et al. |
| 2021/0121246 A1 | 4/2021 | Gudalo |
| 2021/0128254 A1 | 5/2021 | Geric et al. |
| 2021/0169578 A1 | 6/2021 | Calloway et al. |
| 2021/0169581 A1 | 6/2021 | Calloway et al. |
| 2021/0174956 A1 | 6/2021 | Mcginley et al. |
| 2021/0192759 A1 | 6/2021 | Lang |
| 2021/0193681 A1 | 6/2021 | Baek |
| 2021/0196381 A1 | 7/2021 | Eckert et al. |
| 2021/0196383 A1 | 7/2021 | Shelton, IV et al. |
| 2021/0203889 A1 | 7/2021 | Fung et al. |
| 2021/0205020 A1 | 7/2021 | Shelton, IV et al. |
| 2021/0212717 A1 | 7/2021 | Yates et al. |
| 2021/0236755 A1 | 8/2021 | King et al. |
| 2021/0259789 A1 | 8/2021 | Wright et al. |
| 2021/0264680 A1 | 8/2021 | Cvetko et al. |
| 2021/0267664 A1 | 9/2021 | Lennartz et al. |
| 2021/0306691 A1 | 9/2021 | Thomas et al. |
| 2021/0307861 A1 | 10/2021 | Hufford et al. |
| 2021/0313052 A1* | 10/2021 | Makrinich ............ G06V 10/764 |
| 2021/0333864 A1 | 10/2021 | Harvey et al. |
| 2021/0346092 A1 | 11/2021 | Redmond et al. |
| 2021/0369394 A1 | 12/2021 | Braido et al. |
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0151704 A1 | 5/2022 | Nikou |
| 2022/0155910 A1 | 5/2022 | Jeong |
| 2022/0160428 A1 | 5/2022 | Murray et al. |
| 2022/0188545 A1 | 6/2022 | Nagar et al. |
| 2022/0237878 A1 | 7/2022 | Tartz et al. |
| 2022/0257333 A1 | 8/2022 | Haider |
| 2022/0261056 A1 | 8/2022 | Motoi et al. |
| 2022/0283631 A1 | 9/2022 | Peng |
| 2022/0287676 A1 | 9/2022 | Steines et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2022/0387128 A1 | 12/2022 | Bail et al. |
| 2023/0038130 A1 | 2/2023 | Cvetko et al. |
| 2023/0072423 A1 | 3/2023 | Osborn et al. |
| 2023/0121709 A1 | 4/2023 | Xu et al. |
| 2023/0157757 A1 | 5/2023 | Braido et al. |
| 2023/0157762 A1 | 5/2023 | Braido et al. |
| 2024/0130795 A1 | 4/2024 | Clayton et al. |
| 2024/0138931 A1 | 5/2024 | Lefauconnier |
| 2024/0176441 A1 | 5/2024 | Yang et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| EP | 3 053 279 A1 | 8/2016 |
| EP | 3 387 982 A1 | 10/2018 |
| JP | 2001029353 A | 2/2001 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | 2016/154557 A1 | 9/2016 |
| WO | WO-2017058617 A2 | 4/2017 |
| WO | WO-2018116247 A1 | 6/2018 |
| WO | WO-2019215354 A1 | 11/2019 |
| WO | 2020/112217 A1 | 6/2020 |
| WO | 2020/180917 A1 | 9/2020 |

(56) References Cited

FOREIGN PATENT DOCUMENTS

WO     WO-2021044136 A1     3/2021
WO     WO-2021146313 A1 *   7/2021  ............. A61B 34/25

OTHER PUBLICATIONS

IEEE Std 802.3-2012 (Revision of IEEE Std 802.3-2008, published Dec. 28, 2012.

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

Vávra, et al., "Recent Development of Augmented Reality in Surgery: A Review", Journal of Healthcare Engineering, vol. 2017, Article ID 4574172, Aug. 21, 2017, pp. 1-9.

* cited by examiner

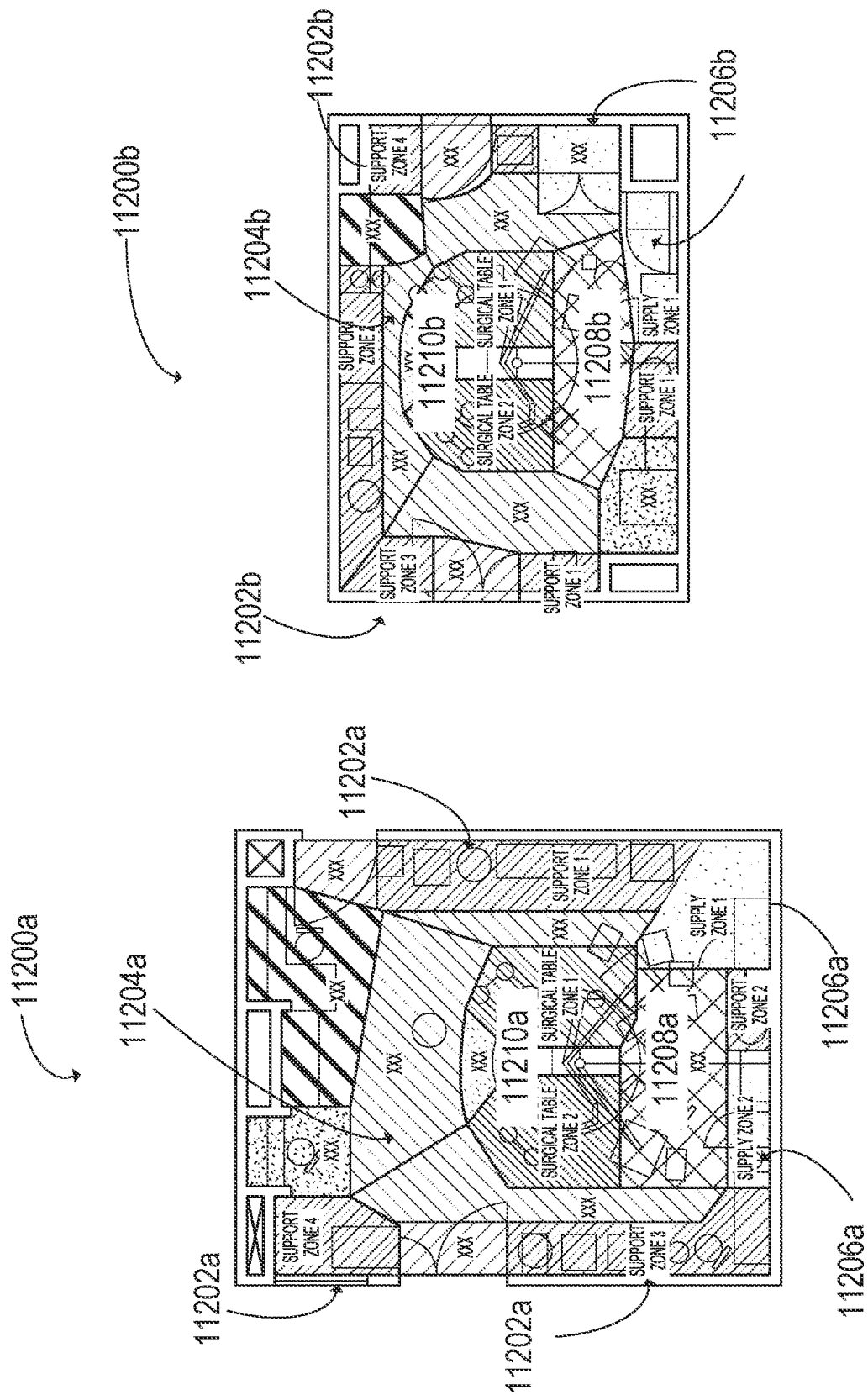

CUSTOMIZATION OF OVERLAID DATA AND CONFIGURATION

CROSS-REFERENCE TO RELATED APPLICATIONS

This application claims the benefit under 35 U.S.C. § 119(e) to U.S. Provisional Patent Application No. 63/174,674, titled HEADS UP DISPLAY, filed Apr. 14, 2021 and to U.S. Provisional Patent Application No. 63/284,326, titled INTRAOPERATIVE DISPLAY FOR SURGICAL SYSTEMS, filed Nov. 30, 2021, the disclosure of each of which is herein incorporated by reference in its entirety.

BACKGROUND

This disclosure relates to apparatuses, systems, and methods for providing an augmented reality interactive experience during a surgical procedure. During a surgical procedure it would be desirable to provide an augmented reality interactive experience of a real-world environment where objects that reside in the real world are enhanced by overlaying computer-generated perceptual information, sometimes across multiple sensory modalities, including visual, auditory, haptic, somatosensory, and olfactory. In the context of this disclosure, images of a surgical field and surgical instruments and other objects appearing in the surgical field are enhanced by overlaying computer-generated visual, auditory, haptic, somatosensory, olfactory, or other sensory information onto the real world images of the surgical field and instruments or other objects appearing in the surgical field. The images may be streamed in real time or may be still images.

Real world surgical instruments include a variety of surgical devices including energy, staplers, or combined energy and staplers. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices are surgical instruments used to cut and staple tissue in a variety of surgical procedures, including bariatric, thoracic, colorectal, gynecologic, urologic and general surgery.

SUMMARY

In various instances, this disclosure provides a method of distributing data among members of a surgical team, the method including receiving imaging data, by a modular control tower, from a plurality of imaging devices, receiving device-dependent data, by the modular control tower, from each of a plurality of intelligent surgical instruments, associating, by the modular control tower, a display device with a member of the surgical team, defining, by the modular control tower, a functional role for the member of the surgical team, and displaying, by the modular control tower, an augmented reality display by the display device. The augmented reality display on the display device includes virtual objects based on the imaging data, the device-dependent data, the functional role of the member of the surgical team, and a surgical activity by the member of the surgical team.

In another instance, this disclosure provides an automated surgical system including a modular control tower, a plurality of imaging devices in data communication with the modular control tower, a plurality of intelligent surgical instruments, and a plurality of display devices in data communication with the modular control tower. Each of the plurality of display devices is associated, by the modular control tower, with one or more members of a surgical team, and each of the one or more members of the surgical team is defined by a functional role. The modular control tower includes a controller in data communication with one or more memory components configured to store instructions that, when executed by the controller, cause the controller to receive imaging data from the plurality of imaging devices, receive device-dependent data from a each of the plurality of intelligent surgical instruments, and display a augmented reality display on each of the plurality of display devices. The augmented reality display on a specified display device may include virtual objects based on the imaging data, the device-dependent data, the functional role of a specified member of the surgical team associated with the specified display device, and a surgical activity by the specified member of the surgical team.

FIGURES

The various aspects described herein, both as to organization and methods of operation, together with further objects and advantages thereof, may best be understood by reference to the following description, taken in conjunction with the accompanying drawings as follows.

Figure 19C:
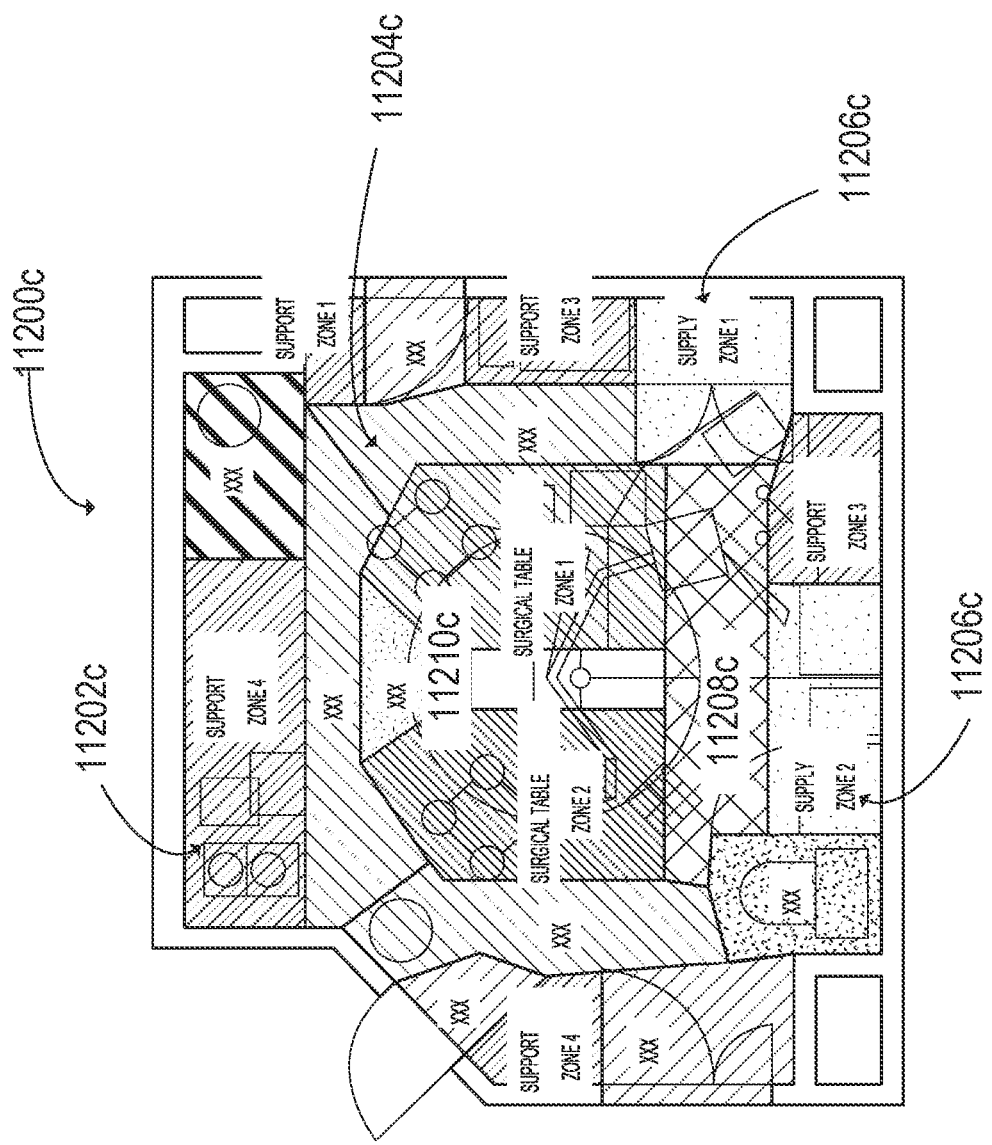

FIG. 19A, FIG. 19B, and FIG. 19C illustrates some exemplary depictions of optimized operating rooms, according to one aspect of this disclosure.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Applicant of the present application owns the following U.S. Patent Applications filed concurrently herewith, the disclosures of each of which is herein incorporated by reference in its entirety:

U.S. patent application Ser. No. 17/688,589, titled METHOD FOR INTRAOPERATIVE DISPLAY FOR SURGICAL SYSTEMS;

U.S. patent application Ser. No. 17/688,597, titled UTILIZATION OF SURGICAL DATA VALUES AND SITUATIONAL AWARENESS TO CONTROL THE OVERLAY IN SURGICAL FIELD VIEW;

U.S. patent application Ser. No. 17/688,605, titled SELECTIVE AND ADJUSTABLE MIXED REALITY OVERLAY IN SURGICAL FIELD VIEW;

U.S. patent application Ser. No. 17/688,615, titled RISK BASED PRIORITIZATION OF DISPLAY ASPECTS IN SURGICAL FIELD VIEW;

U.S. patent application Ser. No. 17/688,626, titled SYSTEMS AND METHODS FOR CONTROLLING SURGICAL DATA OVERLAY;

U.S. patent application Ser. No. 17/688,633, titled SYSTEMS AND METHODS FOR CHANGING DISPLAY OVERLAY OF SURGICAL FIELD VIEW BASED ON TRIGGERING EVENTS;

U.S. patent application Ser. No. 17/688,641, titled INDICATION OF THE COUPLE PAIR OF REMOTE CONTROLS WITH REMOTE DEVICES FUNCTIONS;

U.S. patent application Ser. No. 17/688,646, titled COOPERATIVE OVERLAYS OF INTERACTING INSTRUMENTS WHICH RESULT IN BOTH OVERLAYS BEING EFFECTED;

U.S. patent application Ser. No. 17/688,651, titled ANTICIPATION OF INTERACTIVE UTILIZATION OF COMMON DATA OVERLAYS BY DIFFERENT USERS;

U.S. patent application Ser. No. 17/688,653, titled MIXING DIRECTLY VISUALIZED WITH RENDERED ELEMENTS TO DISPLAY BLENDED ELEMENTS AND ACTIONS HAPPENING ON-SCREEN AND OFF-SCREEN;

U.S. patent application Ser. No. 17/688,655, titled SYSTEM AND METHOD FOR TRACKING A PORTION OF THE USER AS A PROXY FOR NON-MONITORED INSTRUMENT;

U.S. patent application Ser. No. 17/688,656, titled UTILIZING CONTEXTUAL PARAMETERS OF ONE OR MORE SURGICAL DEVICES TO PREDICT A FREQUENCY INTERVAL FOR DISPLAYING SURGICAL INFORMATION;

U.S. patent application Ser. No. 17/688,660, titled COOPERATION AMONG MULTIPLE DISPLAY SYSTEMS TO PROVIDE A HEALTHCARE USER CUSTOMIZED INFORMATION;

U.S. patent application Ser. No. 17/688,663, titled INTRAOPERATIVE DISPLAY FOR SURGICAL SYSTEMS;

U.S. patent application Ser. No. 17/688,667, titled ADAPTATION AND ADJUSTABILITY OR OVERLAID INSTRUMENT INFORMATION FOR SURGICAL SYSTEMS; and U.S. patent application Ser. No. 17/688,671, titled MIXED REALITY FEEDBACK SYSTEMS THAT COOPERATE TO INCREASE EFFICIENT PERCEPTION OF COMPLEX DATA FEEDS.

Applicant of this application owns the following U.S. Patent Applications, the disclosure of each of which is herein incorporated by reference in its entirety:

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;

U.S. patent application Ser. No. 16/209,453, titled METHOD FOR CONTROLLING SMART ENERGY DEVICES, now U.S. Patent Publication No. US-2019-0201046-A1.

During a surgical procedure, a group of medical professionals—a surgical team—work together in a surgical suite or operating room to provide interventional medical care to a patient. Depending on the surgical procedure, each member of the surgical team is tasked with one or more specific roles or functions that, performed together, are designed to render health care to the patient resulting in a favorable outcome. Each member of the surgical team may be tasked to work with one or more pieces of medical equipment that are brought into play during the procedure. The steps and processes involved with the surgical procedure can be complex, and together take significant amount of time to perform. Further, all of the actions of the members of the surgical team must be coordinated for a successful outcome. This coordination of effort requires proper sharing of information throughout the surgical procedure. It can be appreciated that the total amount of information and data, which may change significantly over time, is extensive. Thus, sharing all of the potential surgical information—patient vital sign data, anesthesiology data, data related to the operation of each intelligent surgical device, and similar— could result in overwhelming the members of the surgical team with spurious information. The surgical team members need to keep informed of the data relevant to their specific role and function throughout the surgical procedure, without being subjected to additional data unrelated to their functions.

Disclosed herein is a method and a system using an augmented reality-based surgical system to distribute data to each member of the surgical team based on their specific role or function throughout the course of the surgical procedure.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

Figure 1:
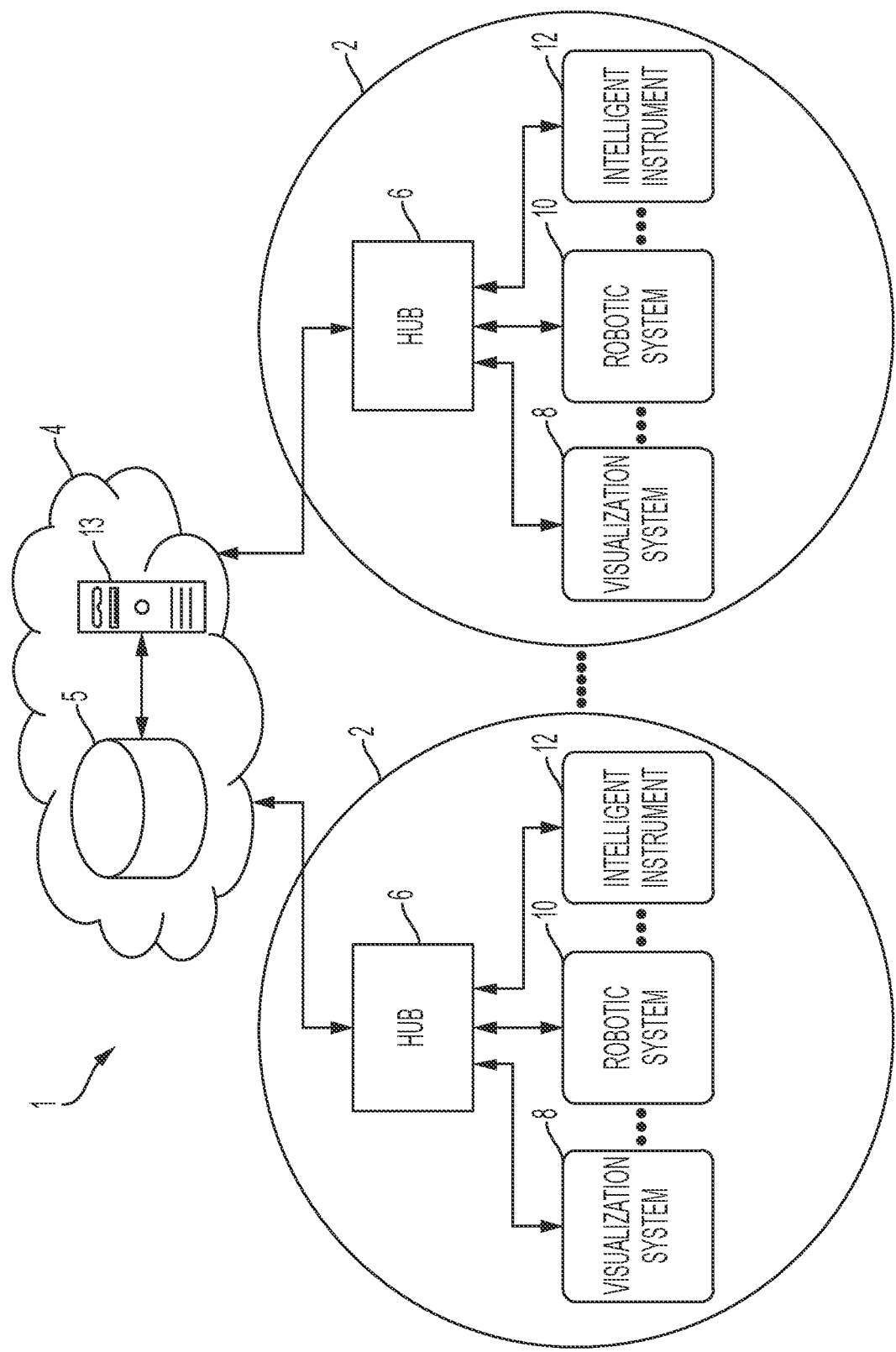
FIG. 1 is a block diagram of a computer-implemented interactive surgical system, according to one aspect of this disclosure.

FIG. 1 depicts a computer-implemented interactive surgical system 1 that includes one or more surgical systems 2 and a cloud-based system 4. The cloud-based system 4 may include a remote server 13 coupled to a storage device 5.

Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
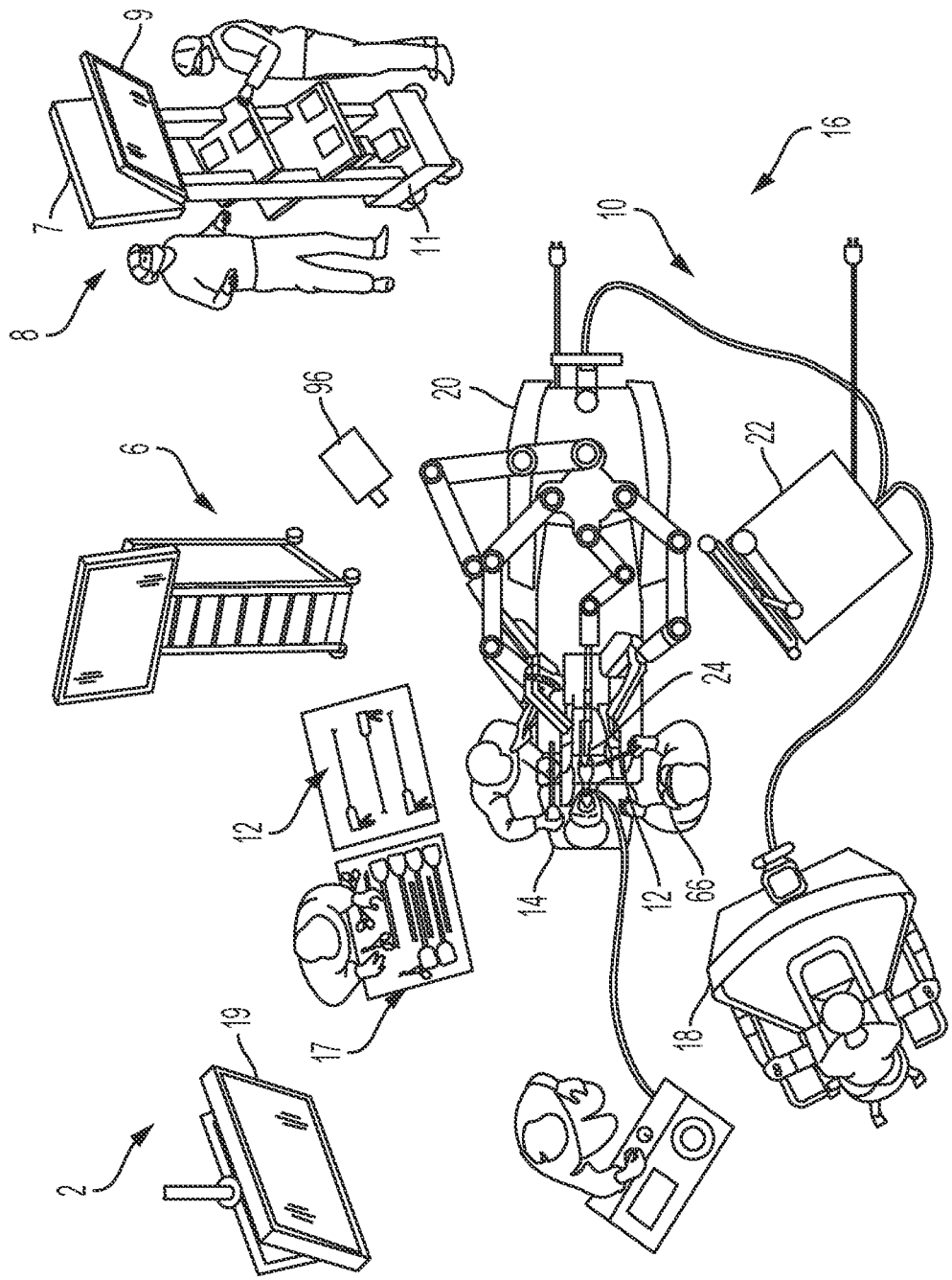
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
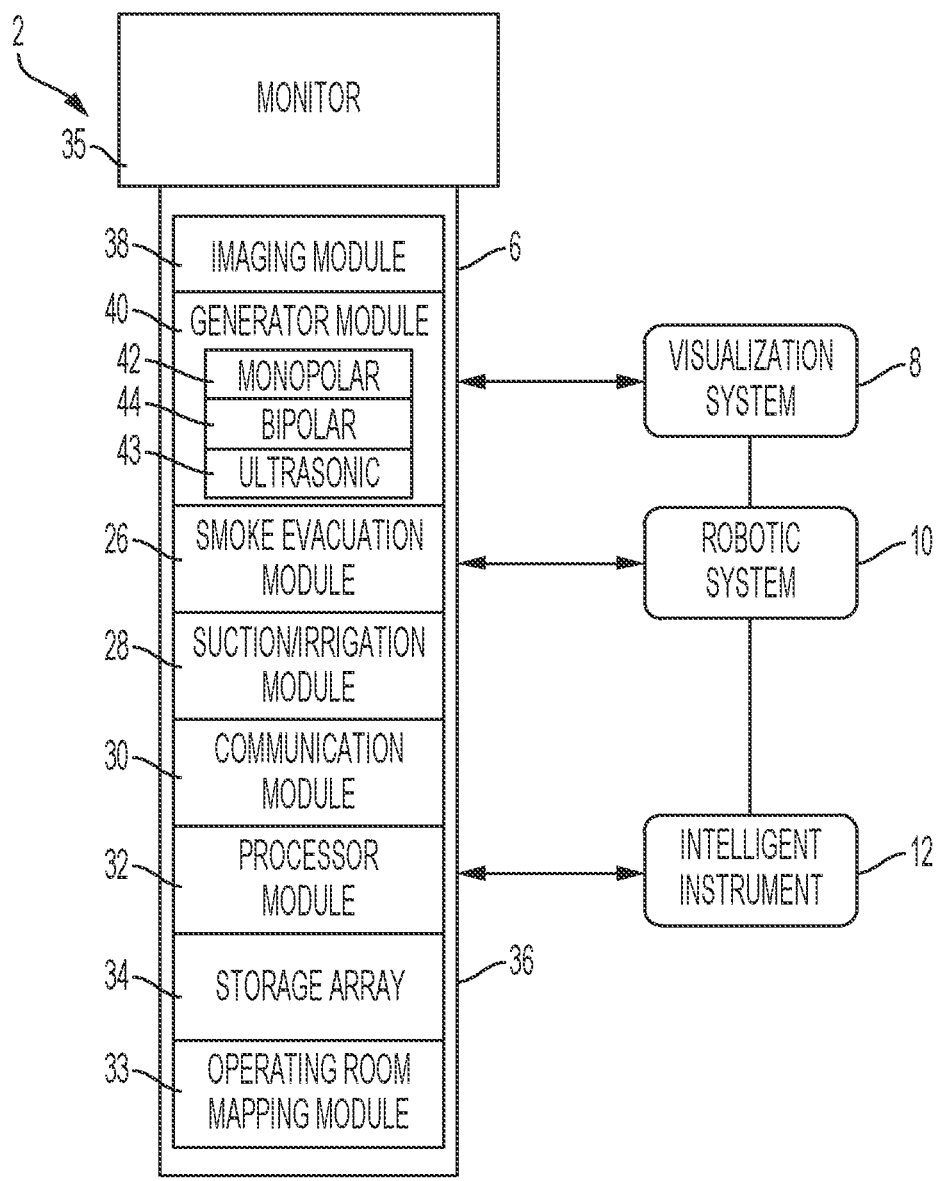
FIG. 3 is a surgical hub paired with a visualization system, a robotic system, and an intelligent instrument, according to one aspect of this disclosure.
Figure 10:
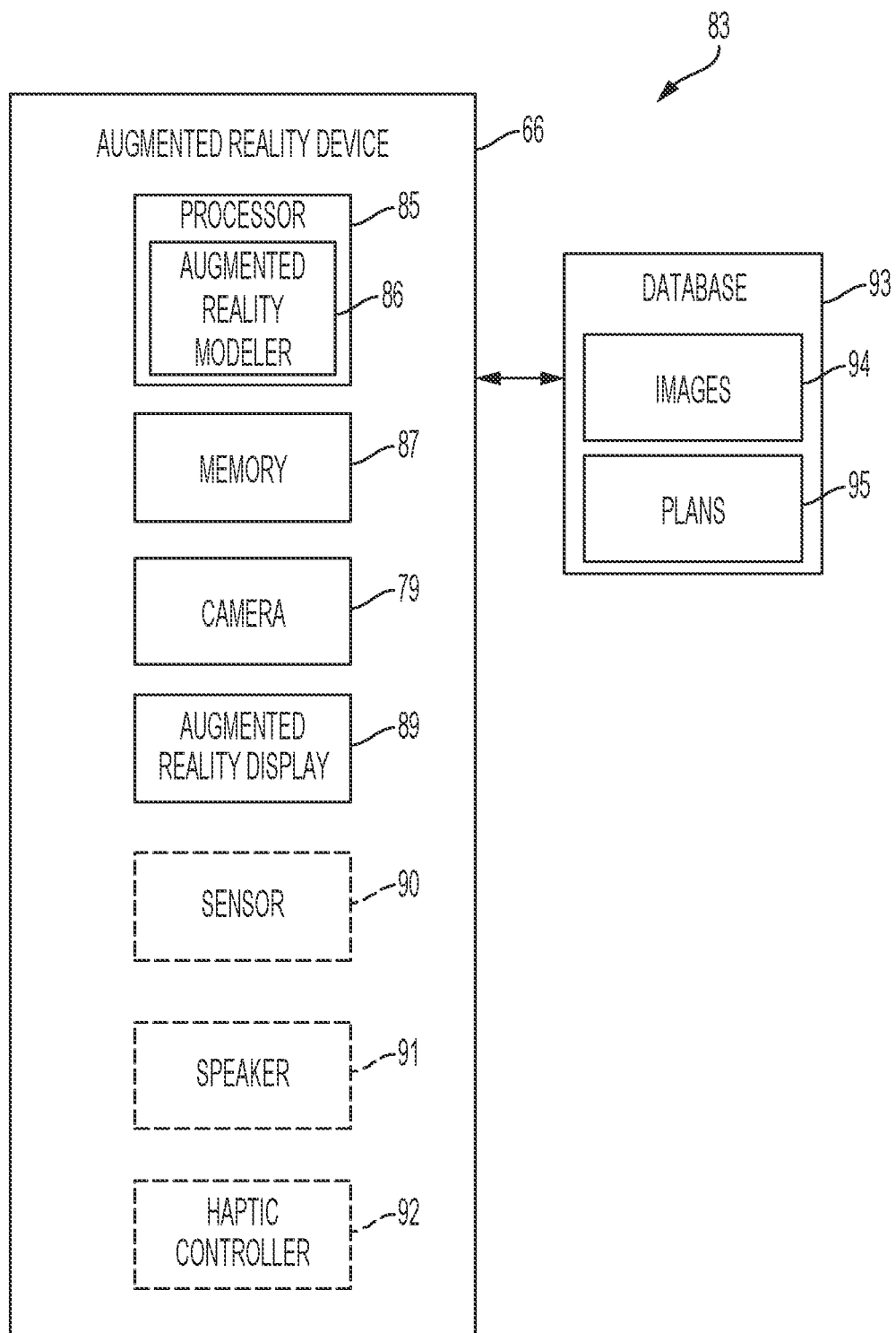
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display 35, an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
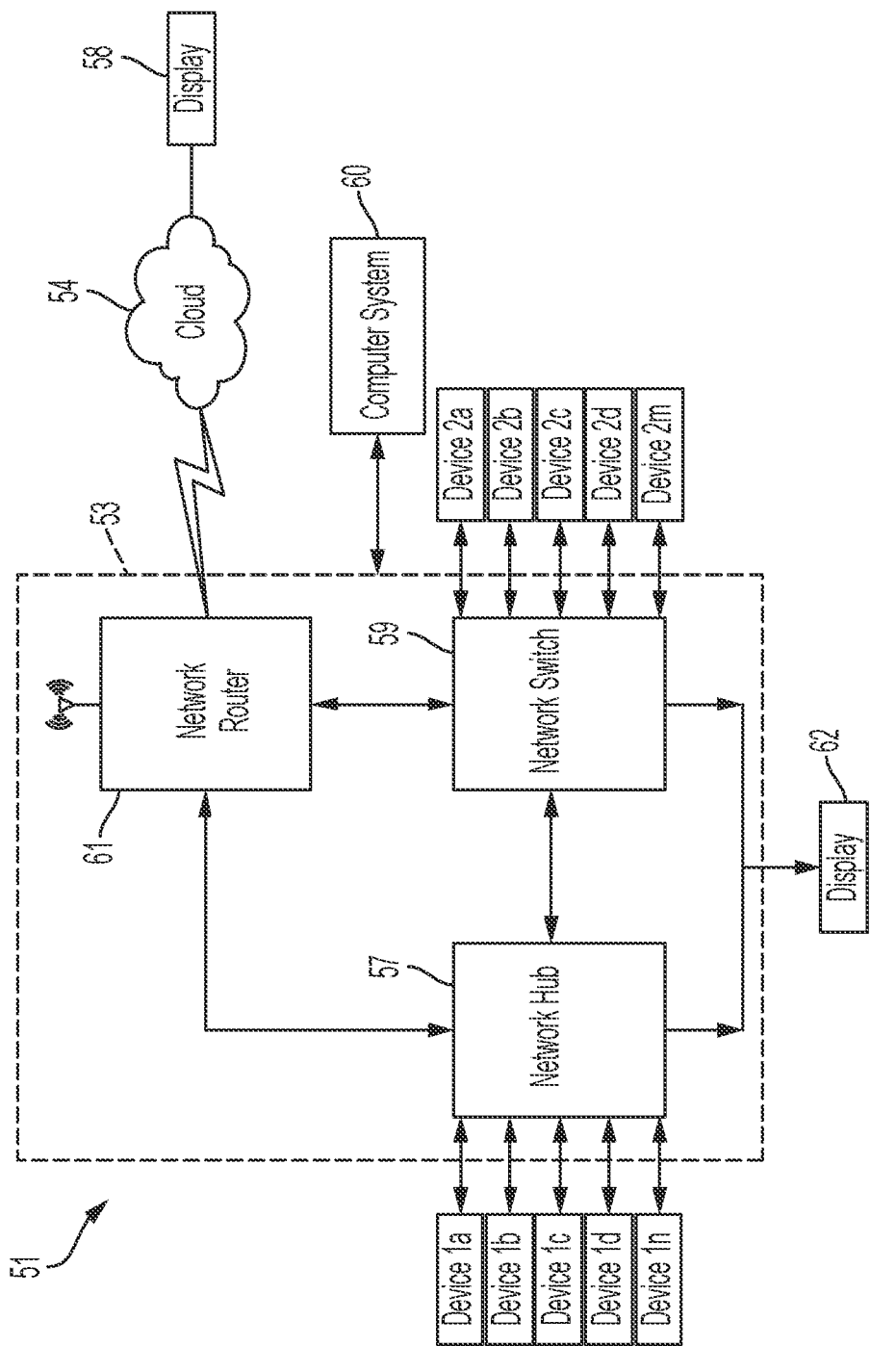
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. 5) coupled to a storage device 55. The modular communication hub 53 comprises a network hub 57 and/or a network switch 59 in communication with a network router 61. The modular communication hub 53 is coupled to a local computer system 60 to process data. Modular devices 1a-1n in the operating theater may be coupled to the modular communication hub 53. The network hub 57 and/or the network switch 59 may be coupled to a network router 61 to connect the devices 1a-1n to the cloud 54 or the local computer system 60. Data associated with the devices 1a-1n may be transferred to cloud-based computers via the router for remote data processing and manipulation. The operating theater devices 1a-1n may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
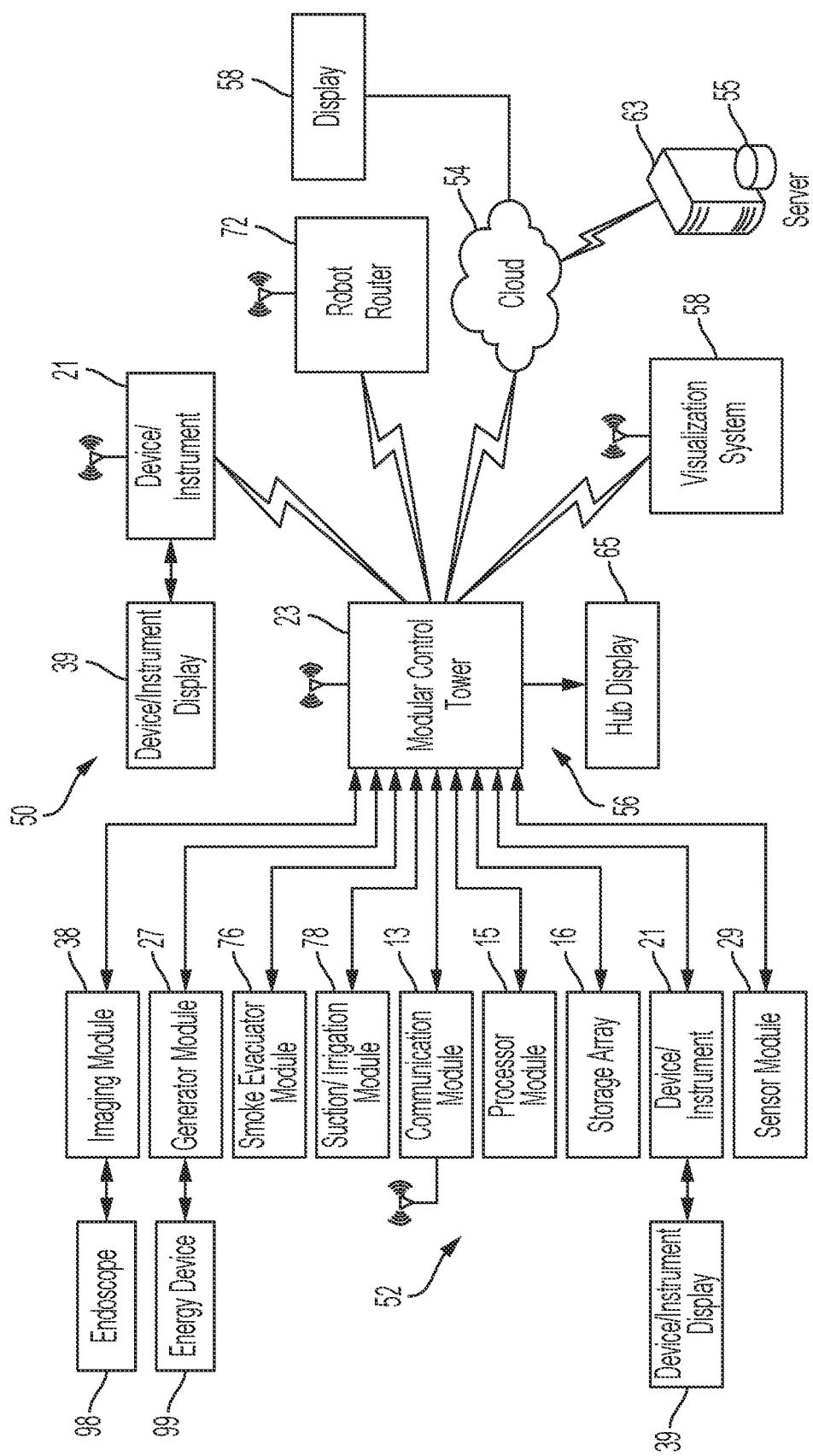
FIG. 5 illustrates a computer-implemented interactive surgical system, according to one aspect of this disclosure.
Figure 6:
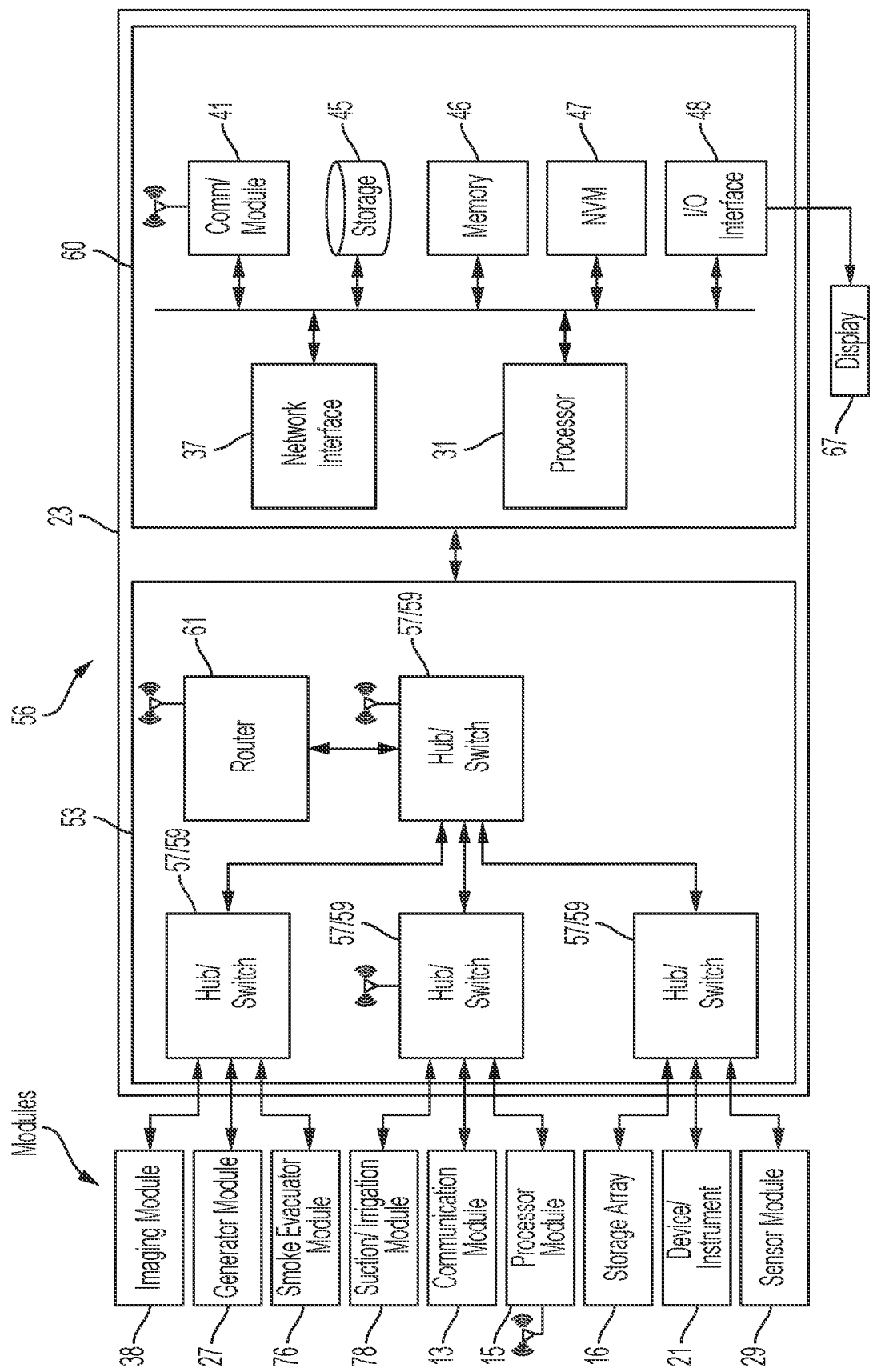
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display 65 also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics processing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

Figure 7:
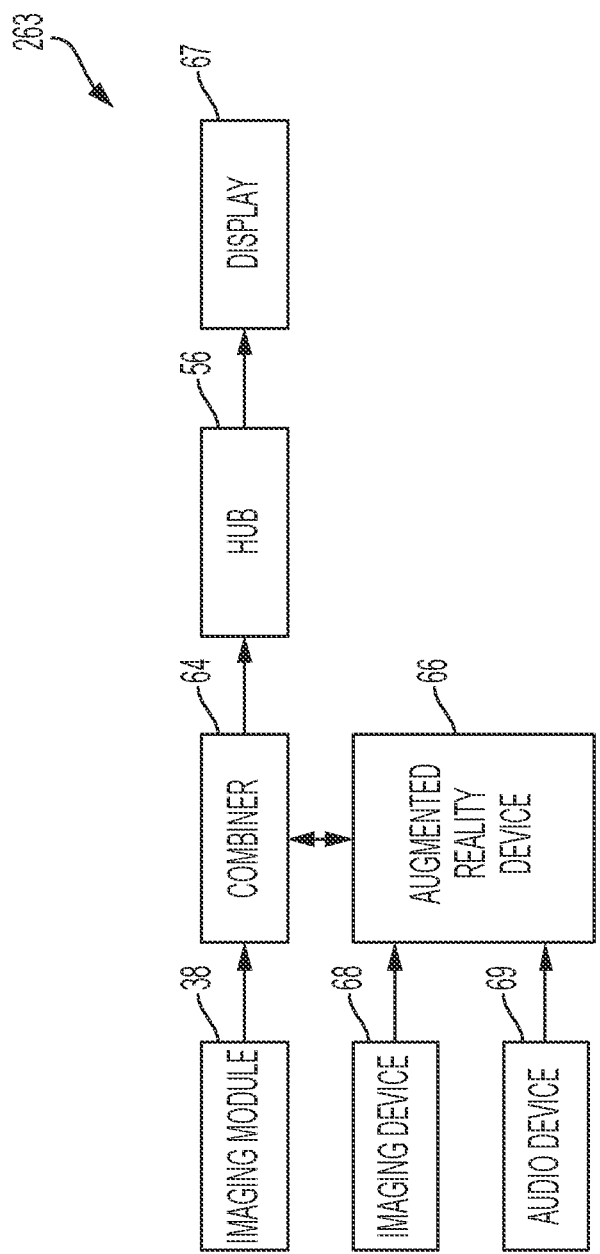
FIG. 7 illustrates an augmented reality (AR) system comprising an intermediate signal combiner positioned in the communication path between an imaging module and a surgical hub display, according to one aspect of this disclosure.

FIG. 7 illustrates an augmented reality system 263 comprising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
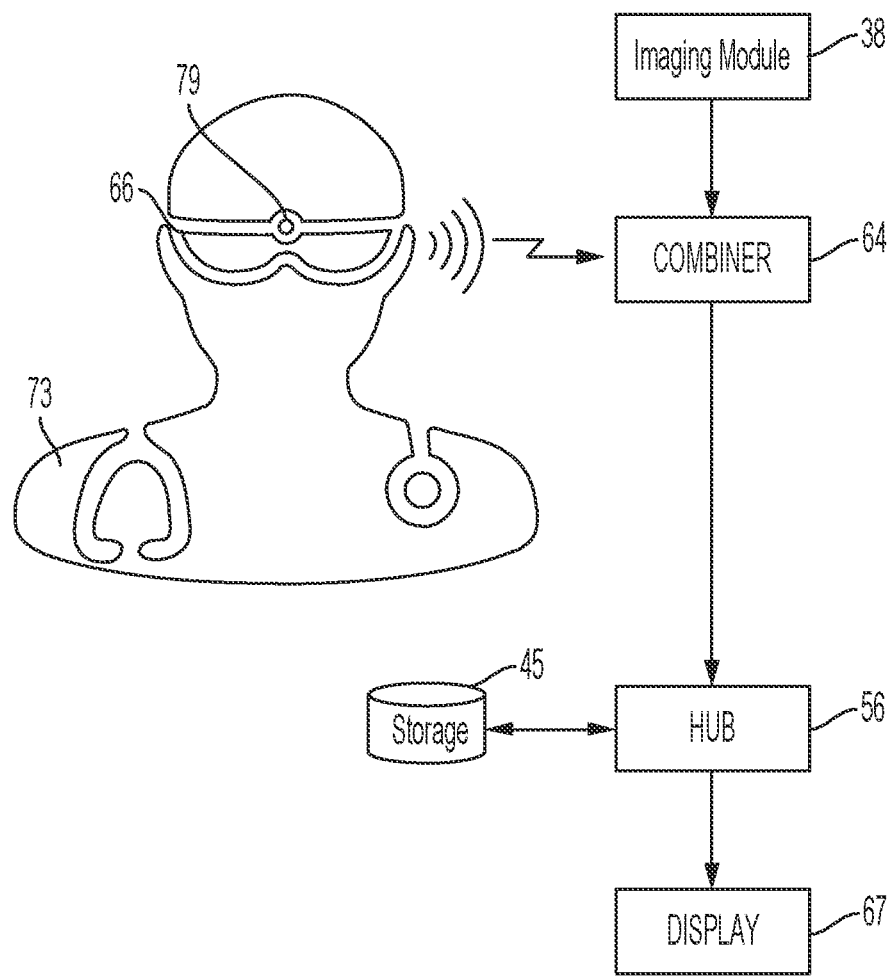
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure— ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
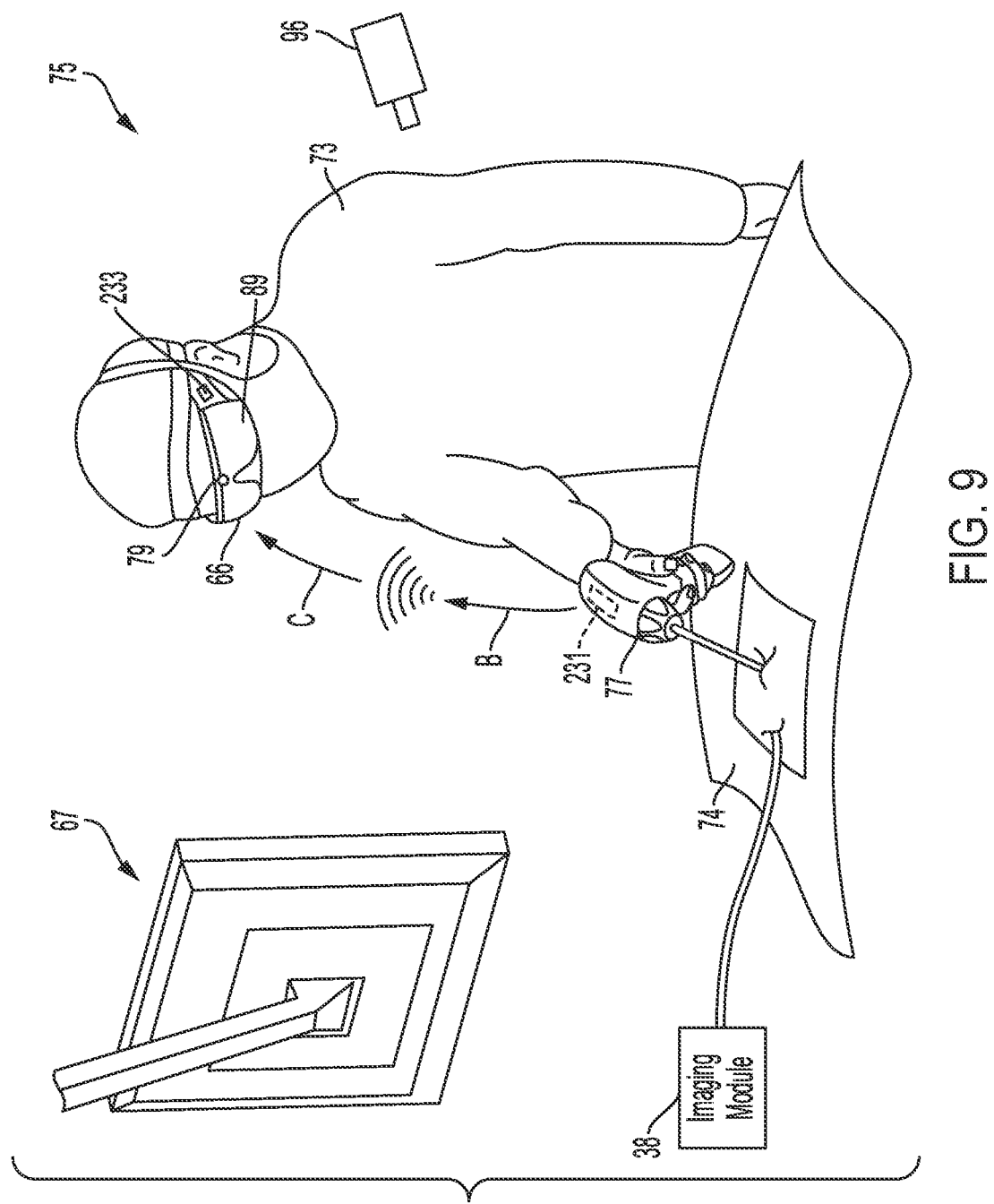
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see different virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66. Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, in accordance with at least one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a HoloLens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IMU (accelerometer, gyroscope), ambient light sensor, proximity sensor functionality. A nebula projects application information on lenses.

In various other examples, the AR device 66 may be any one of the following commercially available AR devices: Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

Figure 11:
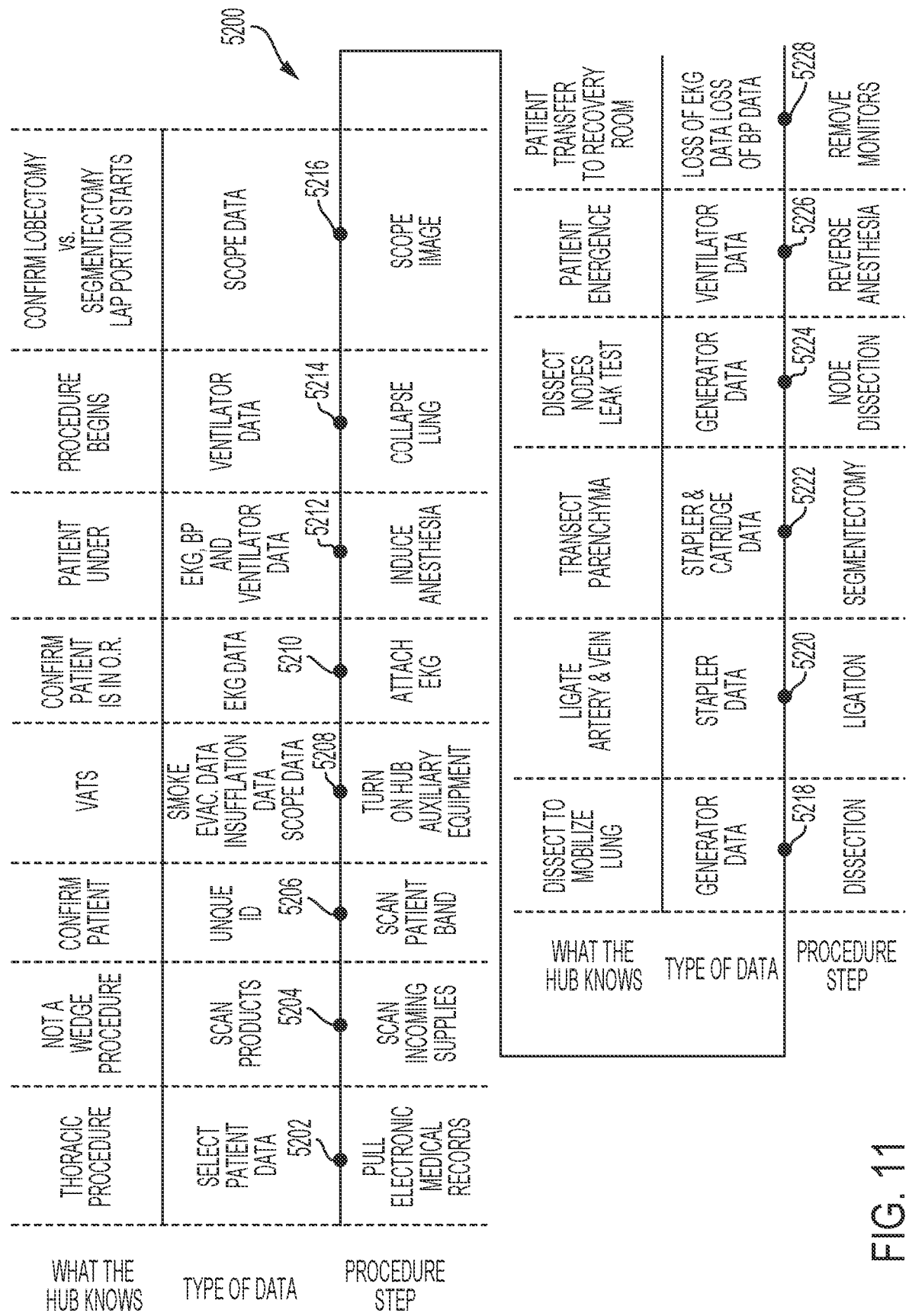
FIG. 11 illustrates a timeline of a situational awareness surgical procedure, according to one aspect of this disclosure.

FIG. 11 illustrates a timeline of a situational awareness surgical procedure. FIG. 11 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 11, the patient data can also be utilized by a situationally aware surgical hub 5104 to generate control adjustments for the paired modular devices 5102.

Augmented Reality Display of Non-Visible Procedure Steps

It may be understood that a computer-implemented interactive surgical system may include one or more surgical systems and a cloud-based system. The cloud-based system may include a remote server coupled to a storage device. Each surgical system includes at least one surgical hub in communication with the cloud. For example, the surgical system may include a visualization system, a robotic system, and one or more handheld intelligent surgical instruments, each configured to communicate with one another and/or the hub. The surgical hub may dynamically determine which devices are in use and the locations of those devices relative to each other and to critical structures and anatomy as identified by the system. Based on the position of these devices, the patient anatomy, and procedural step in the operating room, the augmented reality displays may be updated to depict one or more auxiliary augmented reality views. Such auxiliary augmented reality views may consist of views within the surgical field which the surgeon cannot see in the primary fields of view. In one aspect, such auxiliary augmented reality views may depict anatomical structures that are hidden in the primary field of view by other tissues. In another aspect, such auxiliary augmented reality views may depict views of a handheld intelligent surgical instrument from a secondary point of view (for example an underside view of the handheld intelligent surgical instrument).

It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The surgical system may also retain the imaging information throughout the surgical procedure. The surgical system, through connections to the cloud-based system, may also retain imaging information of the patient's anatomy from previous surgical procedures.

The computer-implemented interactive surgical system may determine the state of the intelligent surgical instruments based on device movement while such devices are in use. Such movement data may be obtained from the intelligent device itself, for example, based on a three-axis accelerometer disposed within the device. Alternatively, the movement data may be obtained from a visualization device that can optically track the motion of the surgical instrument. The interactive surgical system may also include anatomical image recognition algorithms configured to receive imaging data of an anatomical structure and to determine its nature and location. The combination of the motion of the surgical device and the determination of the anatomical structures around the surgical device may be used by the interactive surgical system to identify the current step of the surgical procedure.

In some aspects, the interactive surgical system may use the imaging data regarding the surgical device obtained from the visualization device, to determine if the surgical device is the proper device for the current step in the surgical procedure. The augmented reality device may provide a virtual object as a warning, such as an icon or a text box, overlaying an image of the surgical device in the augmented reality display to provide a warning to the surgical device user that the device is not correct for that procedure.

Figure 12A:
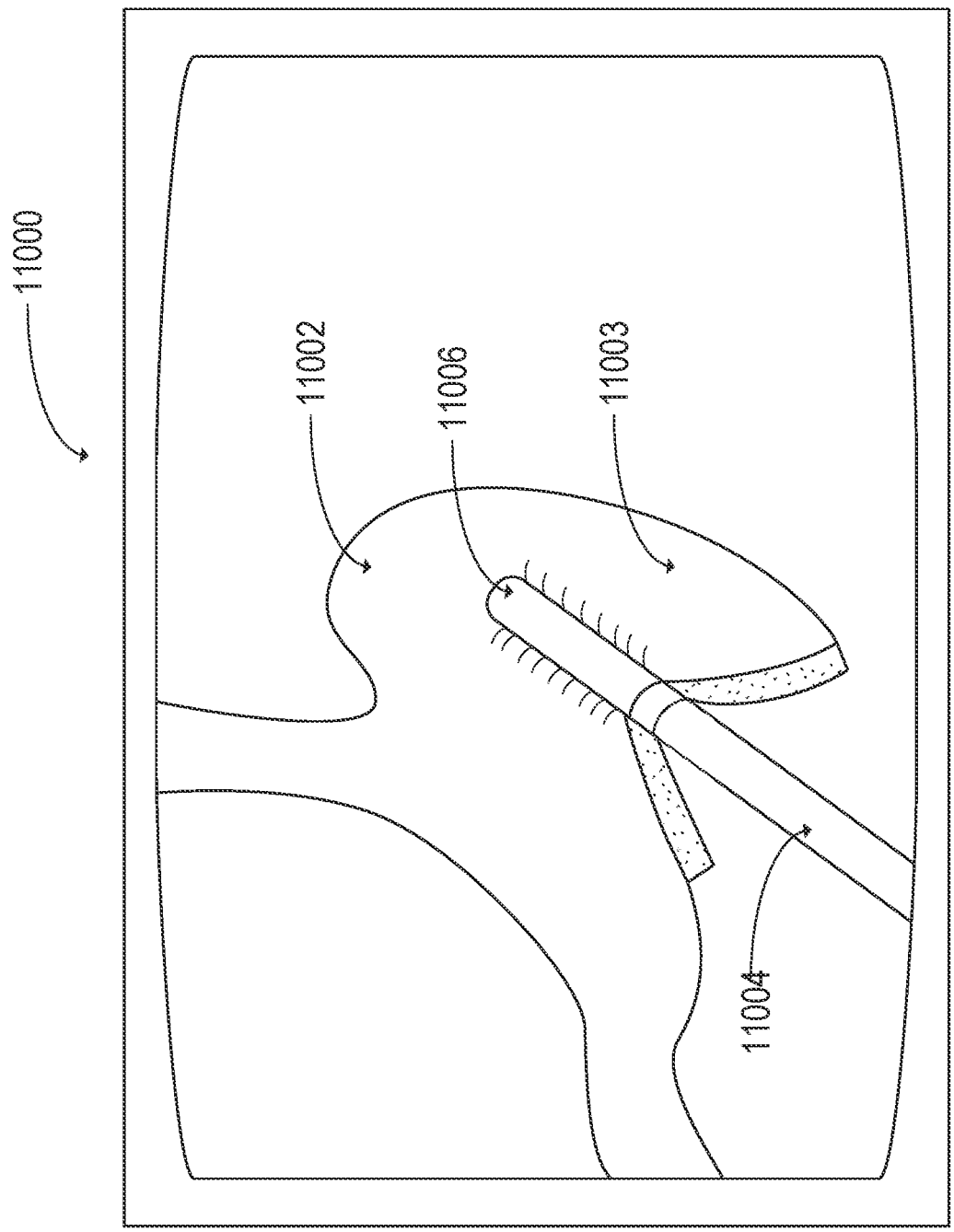
FIG. 12A illustrates a surgical display obtained from a surgical imaging device during a laparoscopic sleeve gastrectomy procedure, according to one aspect of this disclosure.
Figure 12B:
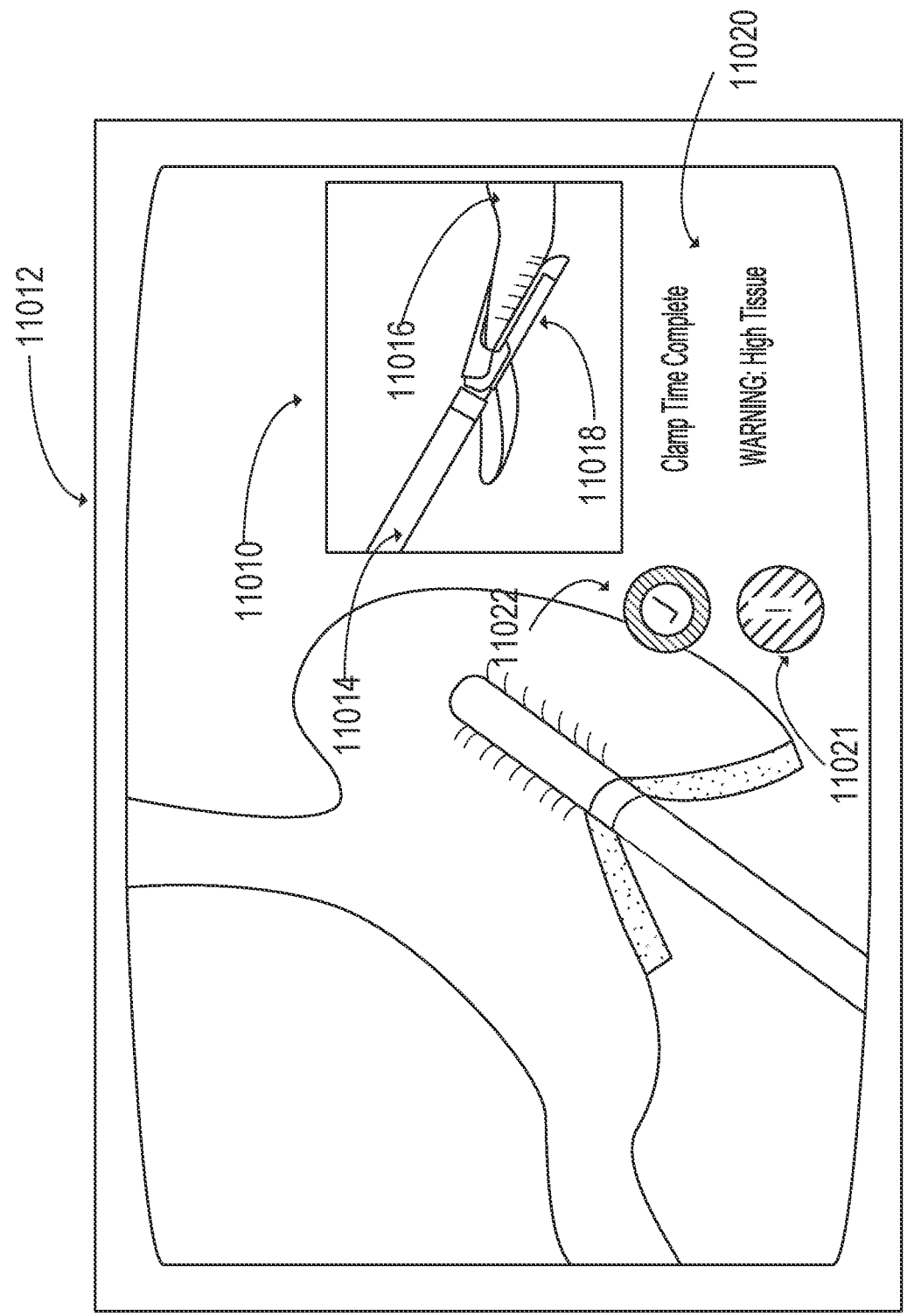
FIG. 12B illustrates an augmented reality image comprising the surgical display along with a virtual secondary view overlaid thereon, according to one aspect of this disclosure.

At steps in which the surgeon is unable to see certain portions of an end effector of an intelligent surgical device, the augmented reality display may include a secondary view generated to show the surgeon the position of the device that cannot be seen in the current fields of view. As an example, FIG. 12A depicts a surgical display 11000 obtained from a surgical imaging device during a laparoscopic sleeve gastrectomy procedure in which a portion of the fundus of a patient's stomach is removed. FIG. 12A depicts the patient's stomach 11002 while a surgeon uses a stapler 11004 to staple an interior edge of the stomach 11002 together and cut the remaining stomach portion 11003 away. As can be observed, the surgical display 11000 depicts a top surface 11006 of the end effector of the stapler 11004. The surgeon may wish to see the bottom side of the stapler 11004 prior to firing the staples, in order to assure that both edges of the resected stomach are sealed together. The surgeon may not wish to rotate the stapler 11004 while it is clamped to the stomach 11002 to see the back side of the device prior to firing. Such a rotation of the stapler 11004 may result in pulling the tissue in ways that may compromise the stapling function. FIG. 12B depicts an augmented reality image 11012 comprising the surgical display 11000 along with a virtual secondary view 11010 overlaid thereon. The virtual secondary view 11010 may include an augmented reality depiction of a side view 11014 of the stapler. The augmented reality depiction of the side view 11014 of the stapler may depict a side view 11016 of a portion of the patient's stomach grasped by a lower jaw 11018 of the stapler. In this manner, the virtual secondary view 11010 can permit the surgeon to visualize the underside of the stapler and see the underside without having to excessively manipulate the tissue.

In some aspects, the augmented reality image 11012 may display information in addition to the imaging views not available to the surgeon (such as the side view 11014 of the stapler and the side view 11016 of the portion of the patient's stomach). For example, the virtual secondary view 11010 may also include visual indicators 11020 regarding the status of the procedure or tissue. For example, a warning 11021 may be depicted indicative of tissue status. In another example, a device status indicator 11022 may indicate a status of the present operation of the stapler.

In one aspect, the virtual secondary view 11010 may be created using predictive modeling of the patient based on previous anatomical images of the patient or images of similar anatomical portions of other patients undergoing the same surgical procedure. In another aspect, the virtual secondary view 11010 may be created from real-time images obtained from a secondary camera used during the procedure. In one example, the surgeon may request the virtual secondary view 11010 from the interactive surgical system through the use of a gesture or spoken command. The interactive surgical system may issue an alert to the surgeon to adjust a position of the secondary camera position so that the auxiliary view can be created.

In another aspect, the virtual secondary view 11010 may be used to identify and display critical anatomic structures at all times during the surgical procedure. As an example, such a persistent secondary view may be used to maintain an image of a tumor disposed on an organ of interest on a display device throughout the surgical procedure. Such a persistent display may allow the surgeon to toggle between overlaying this view on the image of the current procedure and having it as a secondary view on the side of the display.

Predictive Analytics and AI Learning by Procedure—Display Power for Active Devices It may be understood that a computer-implemented interactive surgical system may include one or more surgical systems and a cloud-based system. The cloud-based system may include a remote server coupled to a storage device. Each surgical system includes at least one surgical hub in communication with the cloud. For example, the surgical system may include a visualization system, a robotic system, and one or more handheld intelligent surgical instruments, each configured to communicate with one another and/or the hub. The surgical hub may dynamically determine which devices are in use and the locations of those devices relative to each other and to critical structures and anatomy as identified by the system. Additionally, computer-implemented interactive surgical system and/or cloud-based system may include an artificial intelligence ("AI") system configured to monitor data that is pulled from previous cases of the same procedure type and import data from the current case. Cloud-based data specific to the surgeon operating in a specific surgical case (and/or all completed surgical cases of this type) along with device position data, may permit the AI system to recognizes the current procedure step, and use this information to predict the next step of the procedure. Using this prediction, the augmented reality display may be updated to present the predicted next action to be taken and/or predicted outcomes based on previous cases.

The computer-implemented interactive surgical system may determine the state of the intelligent surgical instruments based on device movement while such devices are in use. Such movement data may be obtained from the intelligent device itself, for example, based on a three-axis accelerometer disposed within the device. Alternatively, the movement data may be obtained from a visualization device that can optically track the motion of the surgical instrument. The interactive surgical system, or the AI system, may also include anatomical image recognition algorithms configured to receive imaging data of an anatomical structure and to determine its nature and location. The combination of the motion of the surgical device and the determination of the anatomical structures around the surgical device may be used by the interactive surgical system to identify the current step of the surgical procedure.

It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The surgical system may also retain the imaging information throughout the surgical procedure. The surgical system, through connections to the cloud-based system, may also retain imaging information of the patient's anatomy from previous surgical procedures, or imaging information from a different patient's anatomy from related surgical procedures.

In one aspect, data may be sent to a cloud data source configured to store in memory all prior procedural data from additional Hub connected cases. The data may be mined and analyzed to predict the most likely next step to be taken by the surgeon. Non-limiting examples of predictive modeling may use one or more of classification models, regression models, and Markov chain models. The prior procedural data may include imaging data and data obtained from the specific devices while they are used in the procedure. Device dependent data may include, for example, power levels, timing parameters, staple types, device position and orientation data, along with other operational parameters. The surgical cases that are analyzed may encompass any number of related or identical procedures. In some instances, only related cases completed by a specific surgeon performing the procedure may be analyzed. In one aspect, the surgeon performing the current procedure may have an option to choose which prior case(s) should be analyzed as being relevant to the case at hand for making predictive recommendations.

Using the surgeon-specified prediction, the tracked position and orientation of surgical devices in use, and patient anatomy, the augmented reality display may be updated to show a prediction of the next surgical action (for example a predicted position of a stapler for its next stapling operation). It may be recognized that the augmented reality display may be shown on any display device within the operating room or outside of it. In some aspects, the augmented reality display may be displayed on a main or primary display in the operating room. Alternatively, the augmented reality display may be displayed on one or more alternative displays, for example tablet devices, secondary monitors, or even a display device associated with a specific intelligent surgical device such as a device generator display. This prediction may be accompanied with additional device specific recommendations such as predicted staple reload size based on the patient's anatomy, or suggesting the use of a buttress material to reduce leakage based on observations from previous stapler operations, patient disease state, or similar.

Other augmented reality displays may include recommendations related to the use of additional surgical devices that can be used to complete the procedure with improved outcomes. By tracking the procedural steps during an on-going surgical procedure, and comparing those to previously obtained data stored in the cloud system, the intelligent surgical system may also adjust the communication prioritization among the intelligent surgical devices within the hub network. Thus, based on surgical history, a second intelligent surgical device that will be needed after the use of first surgical device may have its communication stream prioritized in anticipation of its use. For example, after all Stapler firings are completed in a gastric sleeve procedure, the communication stream from a needle driver may be prioritized over other devices.

Figure 13A:
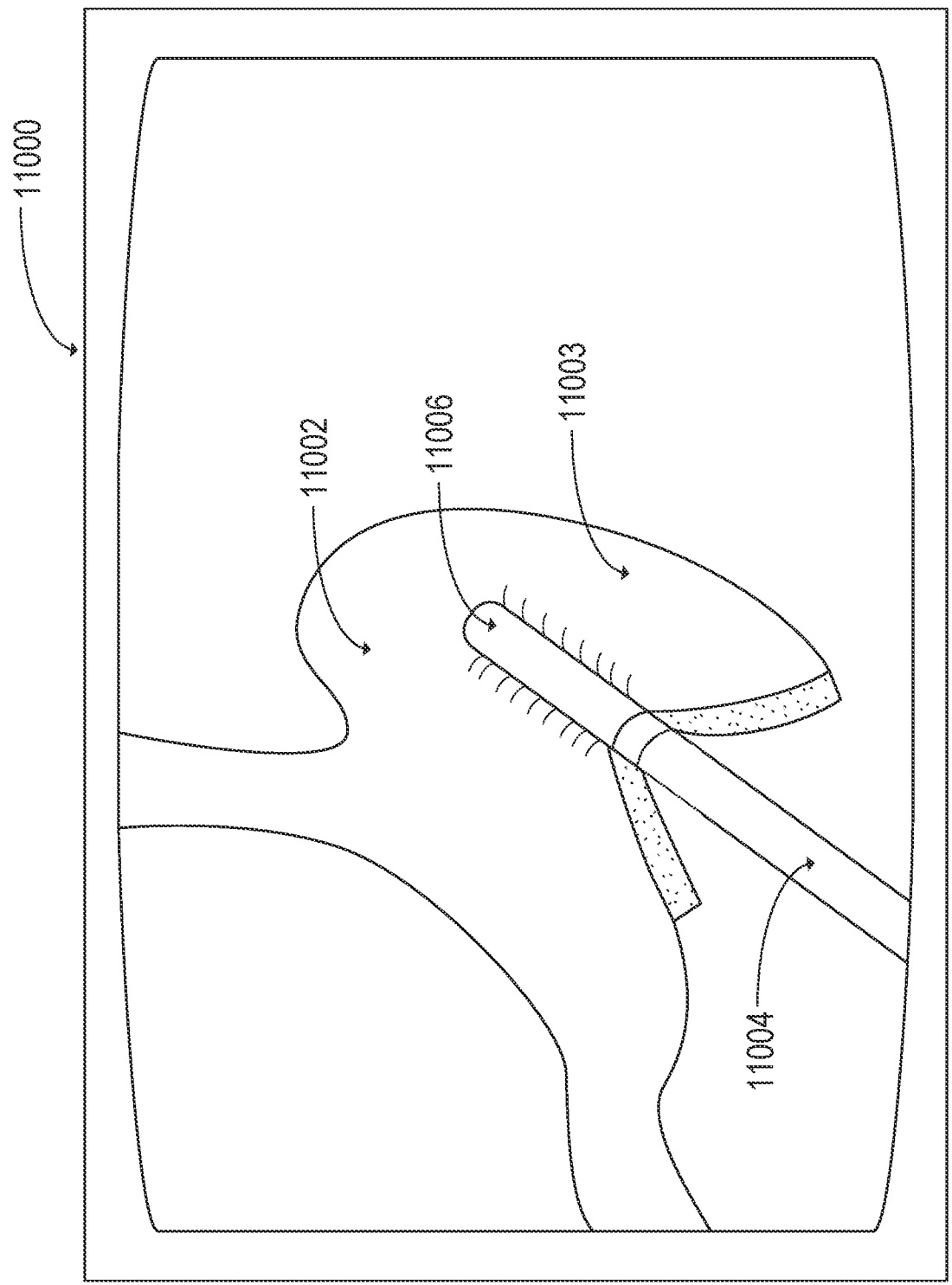
FIG. 13A illustrates a surgical display obtained from a surgical imaging device during a laparoscopic sleeve gastrectomy procedure in which a portion of the fundus of a patient's stomach is removed, according to one aspect of this disclosure.
Figure 13B:
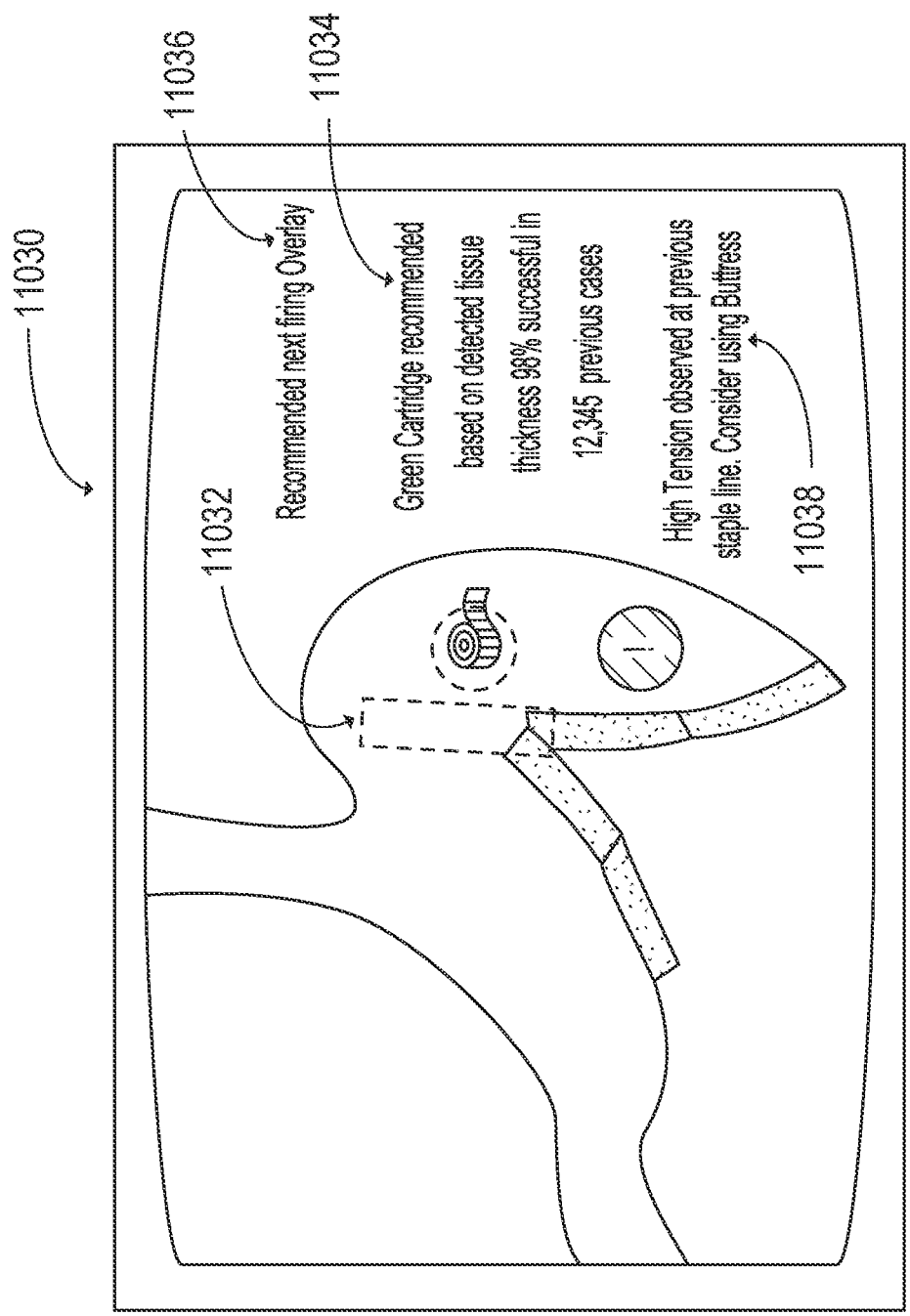
FIG. 13B illustrates an augmented reality image including the surgical display along with a predicted or recommended placement of the stapler, according to one aspect of this disclosure.

As an example, FIG. 13A depicts a surgical display 11000 obtained from a surgical imaging device during a laparoscopic sleeve gastrectomy procedure in which a portion of the fundus of a patient's stomach is removed, similar to the depiction of FIG. 12A. FIG. 13A depicts the patient's stomach 11002 while a surgeon uses a stapler 11004 to staple an interior edge of the stomach 11002 together and cut the remaining stomach portion 11003 away. As can be observed, the surgical display 11000 depicts a top surface 11006 of the end effector of the stapler 11004 at a particular location on the stomach 11002. The surgeon may be uncertain regarding how or where to position the stapler 11004 for the next staple-and-cut operation FIG. 13B depicts an augmented reality image 11030 comprising the surgical display 11000 along with a predicted or recommended placement of the stapler 11032. In some aspects, the augmented reality image 11030 may display ancillary information 11034 in addition to the predicted or recommended placement of the stapler 11032. For example, the ancillary information 11034 may include recommendations 11036 for changes in device operating parameters, such as the type of stapler to be used by the stapler. The recommendation may include statistical data regarding the success rate of the new operating parameters in similar surgeries. In another example, the ancillary information 11034 may also include one or more warnings 11038 regarding the status of the tissue being manipulated by the surgical device. The warnings 11038 may include recommended remediation steps that can be used to address the issue. As an example, the warning 11038 may indicate that a staple line is stressing the tissue which may lead to tearing or incomplete healing at the staple line. A recommendation may be given to suggest the use of a buttress material to help seal the tissue.

Figure 14:
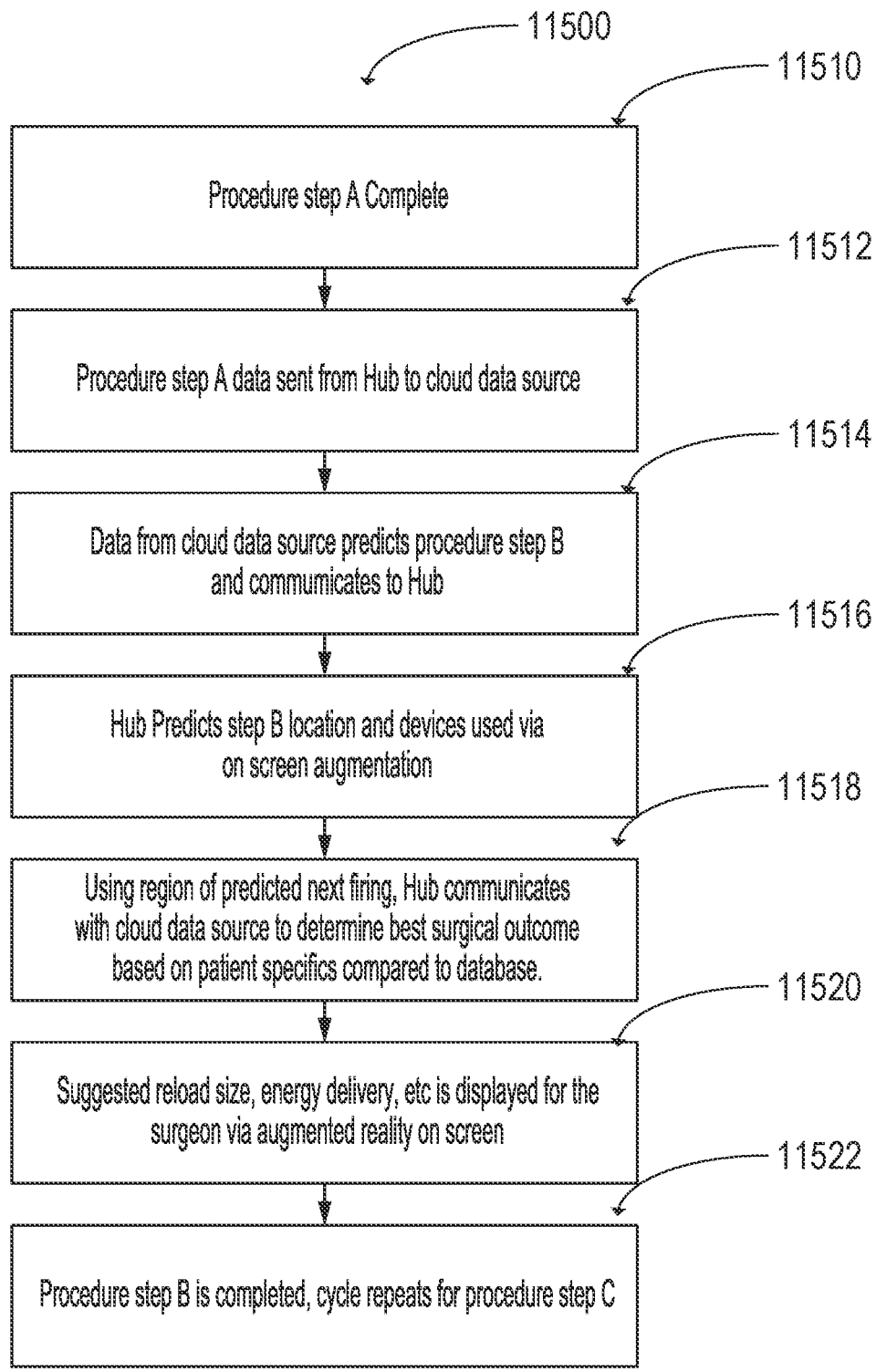
FIG. 14 illustrates a flow chart depicting a method by which an interactive surgical system may receive surgical procedure information and suggest next procedural steps, according to one aspect of this disclosure.

FIG. 14 is a flow chart 11500 depicting a method by which an interactive surgical system may receive surgical procedure information and suggest next procedural steps. In a first step in the process 11510, a surgeon has completed a surgical step A. The data related to surgical step A may be sent 11512 from a communication hub to a cloud-based data source. An artificial intelligence engine in the cloud-based data source may predict 11514 the next step in the surgical procedure, and transmit that data to the communication hub. The communication hub may then predict 11516 a location in the surgical field and the surgical devices that may be used by means of displaying one or more virtual objects on an augmented reality display. The communication hub may then communicate 11518 with the cloud data source to determine a best surgical outcome of the predicted step, location, and device, based on parameters associated with the patient. These parameters may be compared to similar patient statistics, surgical information, and surgical device characteristics in the cloud-based database. The hub may communicate 11520 parameters related to the use, orientation, location, and device parameters to the surgeon as virtual objects displayed on her or his associated augmented reality display device. The surgeon may then complete 11522 the recommended next surgical step. The method may continue in this manner for each subsequent set in the surgical procedure.

Association Instrument and User—Hub/Network Sensing of Devices and Interactions

It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The surgical system may also retain the imaging information throughout the surgical procedure. The surgical system, through connections to the cloud-based system, may also retain imaging information of the patient's anatomy from previous surgical procedures, or imaging information from a different patient's anatomy from related surgical procedures.

The augmented reality interactive surgical system comprises a plurality of data connected intelligent surgical devices. The surgical system can dynamically determine which devices are in use and where those devices are located in space relative to each other and to critical structures and anatomy as identified by the system. Based on the locations of these devices and the preferences/position of the user, the system may prioritize data communication. Data communication prioritization may be enabled for devices proximate to critical structures, and may include increased alert sensitivity at critical procedural steps and/or around specific anatomy. In response to the data communication prioritization, the augmented reality display(s) may be quickly updated to inform the surgeon or other members of the operating room staff of device position, high risk areas, and other sensitive locations.

Via spatial tracking, the interactive surgical system can adapt the augmented reality display to fit procedural steps, such as highlighting critical structures when instruments are nearby, or setting an alert if instruments are too close to each other. Thus, the augmented reality information is constantly tracked by the system, but information is only displayed at the times that it is important to the surgeon. For example, augmented reality visualization of hidden structures may not always be enabled, but may be triggered by a position of the intelligent medical devices. In this manner, the surgeon can proceed with the surgery as normal until high risk areas are identified, or a risk of un-intended injury is present. Under such circumstances, the augmented reality visualization may be enabled and the surgeon is notified of any impending issues.

In one example, the interactive surgical system may recognize the position of a critical anatomical structure, such as the ureter, that may not be otherwise visible to the surgeon. For example, an artificial intelligence module in the cloud system may include anatomical models that may take images of the surgical field and predict or estimate the position of near-by or underlying anatomical structures. Although the ureter may not be readily visible, an image of the ureter may appear as an augmented reality virtual object on one or more augmented reality displays. In one option, such augmented reality virtual objects might be displayed when the system detects/predicts that the end effector of a connected device has come within a specified distance to this critical structure.

In another example, an augmented reality virtual object may include a highlighting superimposed on a display of an end effector of an ultrasound instrument if the temperature reaches a certain level and the instrument is close to the wall of the bowel.

Alternative display options might be based on surgeon preference. Some options could include persistent display of the augmented reality visualization of the critical structure. Alternatively, the display of the augmented reality visualization of the critical structure may be enabled only during a certain portion of the procedure, or only when energy devices are in use. These visualization options may rely on a combination of monitoring device position relative to patient anatomy (via the scope, scans, as examples), processing this information in the interactive surgical system, and enabling the desired augmented reality display based on surgical context.

Figure 15A:
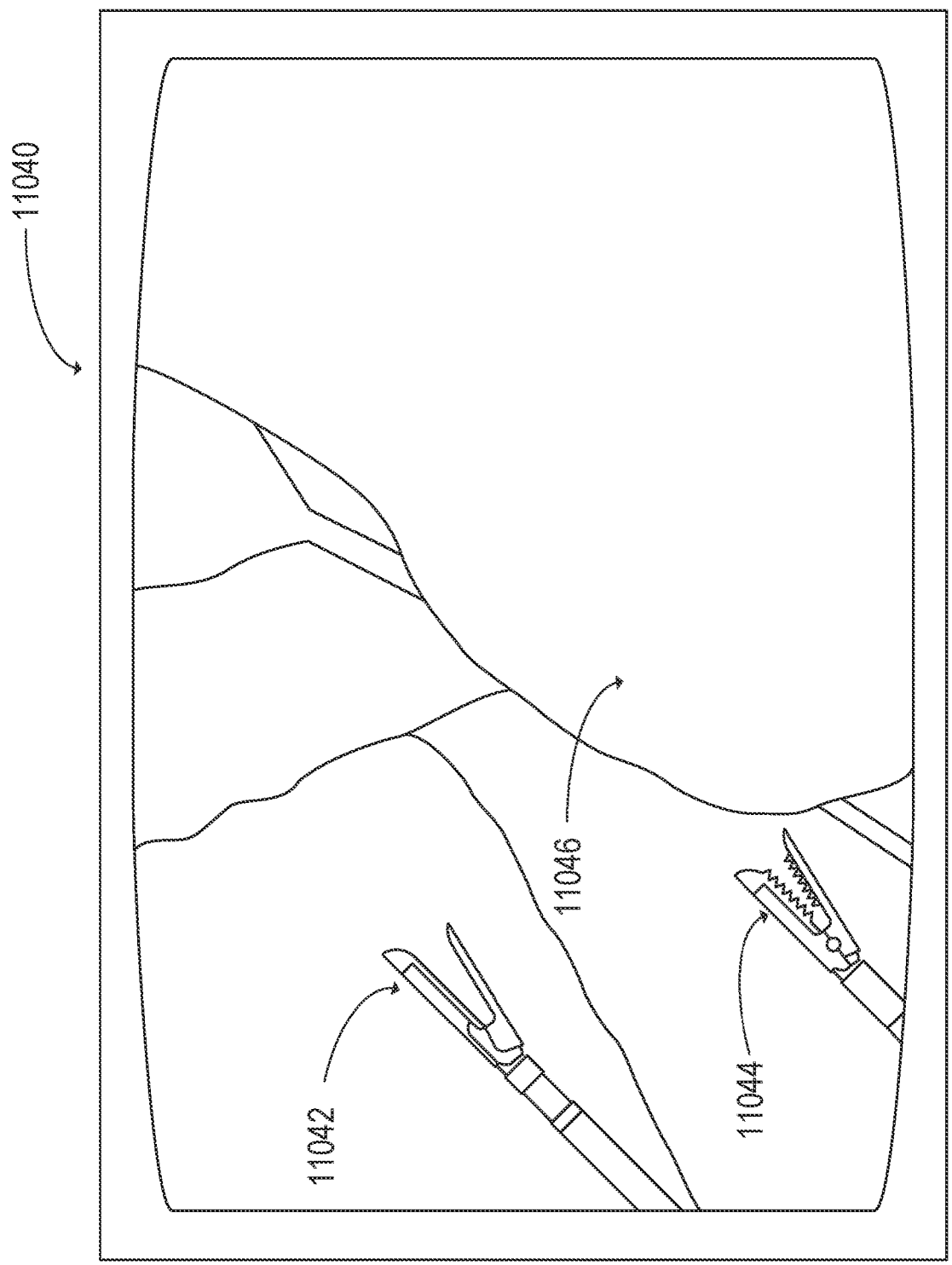
FIG. 15A illustrates a surgical display obtained from a surgical imaging device during a laparoscopic procedure, according to one aspect of this disclosure.

As an example, FIG. 15A depicts a surgical display 11040 obtained from a surgical imaging device during a laparoscopic procedure. The procedure may include the use of an ultrasonic cutter 11042 and an auxiliary tissue clamp 11044. The surgeon may wish to grasp a piece of tissue 11046 with the tissue clamp 11044 and resect a portion of it using the ultrasonic cutter 11042. The surgeon may be unaware that a portion of the patient's ureter lies close beneath the tissue 11046.

Figure 15B:
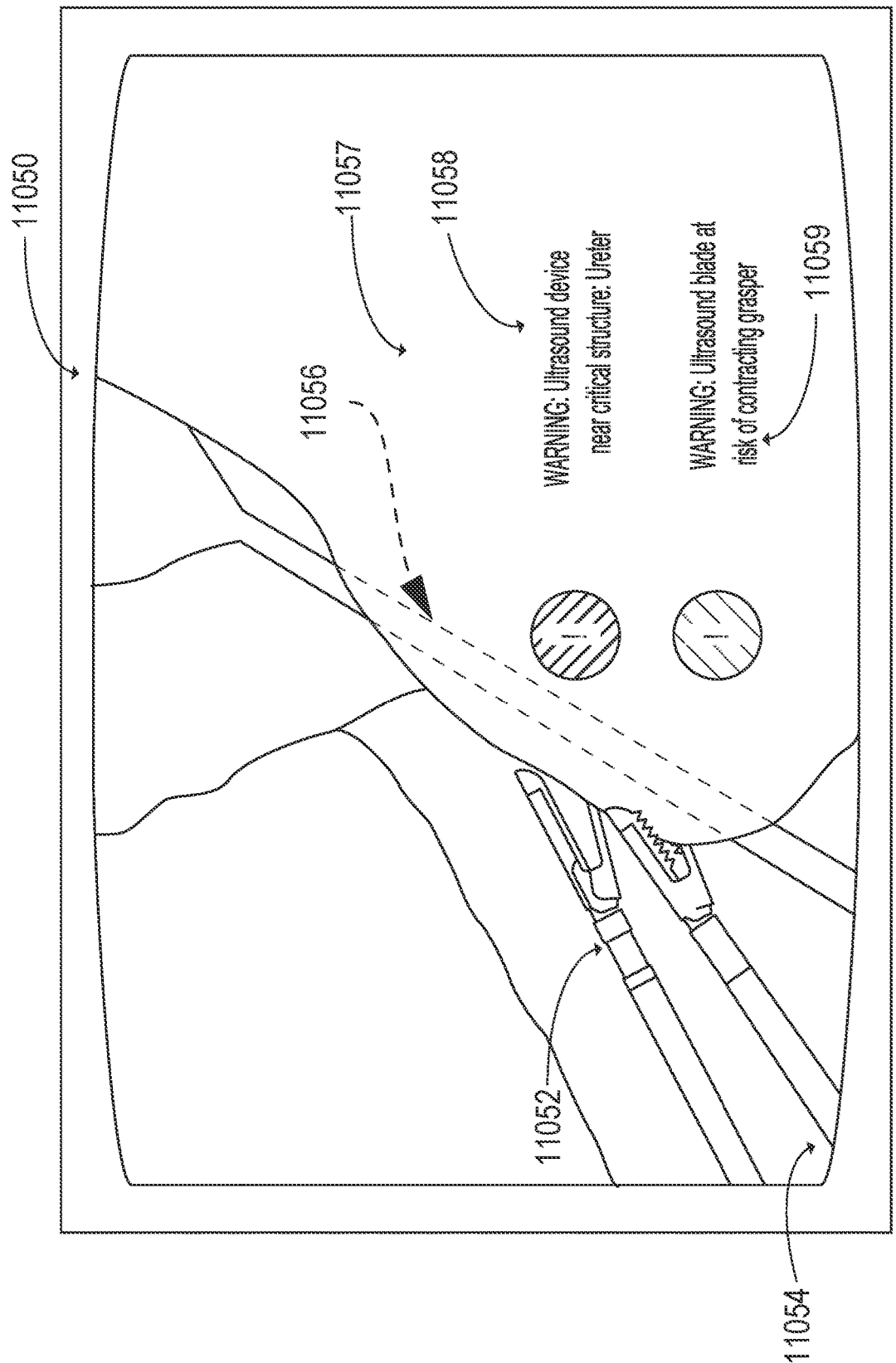
FIG. 15B illustrates an augmented reality image comprising the surgical display along with an augmented reality virtual object presenting an outline of the ureter underlying the tissue to be resected, according to one aspect of this disclosure.

FIG. 15B depicts an augmented reality image 11050 comprising the surgical display 11040 along with an augmented reality virtual object 11056 presenting an outline of the ureter underlying the tissue to be resected. In some aspects, the augmented reality image 11050 may display ancillary information 11057 in addition to augmented reality virtual object 11056. For example, the ancillary information 11057 may include a tissue related warning 11058 that the ultrasonic cutter 11052 or the auxiliary tissue clamp 11054 is too close to the position of the ureter. The ancillary information 11057 may include a device related warning 11059 that the ultrasonic cutter 11052 may be too close to the position of the auxiliary tissue clamp 11054.

The augmented reality displays may be used to provide any related guidance to a surgeon related to the procedure or the device being used in the procedure. For example, a surgeon-in-training (such as a surgical resident) may receive a greater amount of feedback in a user training mode if the interactive surgical system determines that the surgeon=in-training lacks experience based on the surgeon's skill history. The amount of feedback presented may be graded based on a "training curve" related to the skill level of the surgeon, and may be accelerated if the surgeon displays an improvement in the learned skills. The feedback may be tailored to present guidance in areas needing skill improvement. The individualized feedback may be based on data and images stored in the cloud system for the individual surgeon based on past performance and surgical experience and the recorded use by the surgeon of the device during past surgeries. Examples of surgical outcomes that may indicate a need for skill improvement may include bleeding at the surgical site, double burns for cauterized tissue, or tissue tagging.

The augmented reality displays may also be used to recommend specific devices to a surgeon during a procedure. Improved, or updated devices may be recommended to replace the surgical device being used during the procedure. Information may be provided in the augmented reality display indicating how such an improved device may be used in the present surgery. The augmented reality display may also provide statistics regarding the outcomes of similar surgeries performed with the recommended device compared to the outcomes of surgeries using the present device.

Linked Users to Form an AR Ecosystem

It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The augmented reality interactive surgical system comprises a plurality of data connected intelligent surgical devices and one or more display devices configured to provide the members of the surgical team information related to the surgical operations, the patient status, and the operation of the intelligent surgical devices used throughout. The surgical system can dynamically determine which devices are in use and where those devices are located in space relative to each other and to critical structures and anatomy as identified by the system.

In some aspects, each member of a surgical team may be associate with on one or more display devices to provide information related to the surgical proceedings. Each display device may display images obtained from one or more imaging devices along with augmented reality virtual objects overlaid on the imaging data. The display associated with any member of the surgical team may be customized to the functional role of that surgical team member. For example, the display of a member of the surgical team may be customized to include virtual objects associated with a device or instrument controlled by the member of the surgical team. The interactive surgical system may monitor the instruments and devices under the control of each surgical team member within the operating room. The data displayed on each display device may be dependent on which user has control of a surgical device and the surgical role of the user. The displayed information for a user may change as instruments or devices enter or leave their control. For example, the surgical system may track instrument exchanges between surgeons or between surgeons and nurses. The augmented reality displays may adjust the nature, type, and/or positions of the virtual objects in the augmented reality displays associated with the affected surgical team members. For example, virtual objects associated with control of a surgical device may disappear from a display associated with one surgical team member as she or he relinquishes control of the surgical device. Similarly, virtual objects associated with control of the surgical device may appear on a display associated with a second surgical team member as she or he accepts control of the surgical device.

In some aspects, the intelligent surgical system may be capable of determining an in-situ and an extracorporeal aspect of the instruments in use and the associated user in control of the instruments. The surgical system may also be able to associate actions occurring outside the body with motions occurring inside the body to verify correct correlation of the two facets.

As disclosed above, each member of the surgical team may have associated with her/himself display device configured to display augmented reality displays customized to the activity and role of the surgical team member. Such displays may include any appropriate type of display, including a primary or main operating room display, one or more auxiliary operating room displays, displays associated with one or more tablet devices, a laptop display, smart phone displays, or displays associated with individual surgical devices such as patient monitoring devices or anesthesia delivery/monitoring devices. The purpose of each of these devices is to provide information customized to the functional role of the individual.

Not only is a display customized to a specific surgical team member, but the team member may be able to modify her or his display to show the display of another member of the team, such as by swiping a touch activated screen, the use of a hand gesture, or by a verbal command. In this manner, the team member may be able to "pull" the display from another team member's display device. Alternatively, some team members may have authority to "push" their own display onto the display device of other members of the surgical team.

In some aspects, each member may not have a physical display device. Instead, multiple members of the surgical team may rely on a shared or common display device. In this circumstance, the customization experience may be derived from a wearable image filtering device such as glasses, a heads-up display, or contact lenses. The common display device may display an image including the virtual objects associated with all of the members of the surgical team. The virtual objects may be color coded or otherwise visually encoded so that each member of the surgical team may be able to view only those virtual objects associated with her or him by using a wearable image filtering device. The wearable image filtering devices may filter an image displayed on a common display device based on color filtering, polarization filtering, or time filtering of a rapidly changing imaging. Color and polarization filtering may allow a user to see only light emitted at preselected wavelengths or polarization states. Time filtering may coordinate the timing of a blanking condition of the wearable filter with the time a specific image is displayed on the common display device. Color filter contact lenses or goggles may be used for rapid prototyping and information gathering on information level. Alternatively, zoom feature or UV light activation options may be incorporated in the wearable filters.

The interactive surgical system may also manage the priority of the communications among and between the members of the surgical team and/or with the hub or cloud system. Thus, communications arising from functions or activities deemed critical to the procedure at any specified time may have priority over communications that may, for example, be associated with routine patient monitoring. These communications may be prioritized among the members of the surgical team. Thus, relevant data generated by critical devices being used during a specific portion of a procedure may be communicated directly to all relevant members of the surgical team to convey device useful information. In one non-limiting example, a surgeon may always needs to know if an ultrasonic blade is hot but an anesthesiologist may only need to know when the hot blade comes in contact with a critical anatomical structure. In this case, the anesthesiologist may be notified by vibrational feedback associated with the temperature of the ultrasonic blade only when a critical anatomical structure is contacted with by hot blade. The surgeon may receive tactile feedback—for example, a light vibrational response—from the hot blade and receive notification/light vibration when the blade is close to critical structures overall. As another example, devices and/or procedures that result in difficulty with hemostasis may be prioritized. Data specific portion of the procedure that may be necessary to monitor hemostasis—type and source of blood flow, for example—may be shared among the surgical team.

While each member of the surgical team may have her or his own customized augmented reality display, under some circumstance, the individual display options may be overridden. As one example, during emergency situations, everyone may see the same display or gets the same prioritized alerts based on detected situation. Every member of the surgical team may get a standard non-negotiable master settings or view that is standard. However, each individual may add additional settings and preferences to the standard image.

In some aspects, communications between specific members of the surgical team may be prioritized to result in pairing information with specific members for direct communication. In one example, a head surgeon can share what she or he is seeing and her or his display/wearable preferences may be extend to specifically chosen members of the surgical team. For example, the head surgeon may "push" her or his display to a surgical resident who can thus see or feel the same things as the head surgeon. A ping system with a wearable device may notify other surgical team members to switch over their respective augmented reality displays. As one example, a surgeon or physician assistant may ping an anesthesiologist to switch to their view/preferences to that of the surgeon. It may be understood that a surgical team member thus pinged may decline the invitation if a higher priority task is at hand.

The surgical system may initiate a communication pairing with an intelligent surgical device and subsequently associate a user of the device with the device while it is active. It is disclosed above that an intelligent surgical device may be controlled by a member of surgical team. The interactive surgical system may recognize the associating of the person with the device after the interactive surgical system has established a communication pairing with the device itself. The system may first determine that the device is located within the surgical suite. The system may then recognize when the device is removed from its sterile packaging, thereby becoming passively selectable for use by a member of the team. Once a surgical team member begins to handle the device, the interactive surgical system may then recognize the status of the intelligent device as being actively selected and the system may then recognize a control or associating between the device and the surgical team member.

Monitoring Device-User Interactions and Changes in Display Needs

The interactive surgical system may determine a task of a member of the surgical team based on one or more of the situational awareness of the intelligent surgical instrument status, the team member's functional role, and the step in the procedure. The situational awareness may be used to adapt the augmented reality virtual object display information based on the task at hand.

In one non-limiting example, the surgeon may deploy a loaded stapler positioned on the organ to transect. The augmented reality display may include a virtual object displaying information related to one or more of a force-to-fire (FTF), a wait time, and a tissue tension detected, as well as a cartridge color, status, and stroke location of the intelligent medical device. Once the firing is complete, the surgeon could release the tissue, close, and remove the device. Since the device now has an expended cartridge, the augmented reality display could indicate the inability of the stapler to be used again until reloaded. The augmented reality display may use a colored virtual object as an overlay over an image of the stapler to indicate that it is not available for additional use until the staples are reloaded. As the stapler is handed off to the scrub nurse, the virtual object representing the stapler could be transferred to the nurse's augmented reality display. At the same time, the virtual object representing the stapler could be removed from the surgeon's augmented reality display to indicate that control of the device has been passed to the nurse. The nurse's augmented reality display could then indicate fired state of the stapler, and indicate the steps needed to reload the instrument with a fresh unfired cartridge. Such virtual objects may include indications regarding buttons of the stapler to press, their order, and a suggestion of the next cartridge color based on the awareness of the procedure plan and the step in which the intelligent medical instrument is currently in-between. In some aspects, the nurse's augmented reality display could also link up to other displays to show where the needed cartridge is located and even a compatibility of the cartridge being loaded with the device and the procedure.

In some aspects, the interactive surgical system may track multiple aspects of an operating room procedure. In some examples, the interactive surgical system may track the use and control of the multiple intelligent surgical devices used during the procedure, the location and activities of the surgical team members, and the disposition of the equipment and patient within the confines of the operating room itself. Additional trackable aspects that the interactive surgical system may include surgical access points and register them with patient, instrument location, orientation, or status, or missing or misplaced equipment. In some additional aspects, the interactive surgical system may identify surgical procedural steps in process. The surgical system may display virtual objects with a background highlight on one or more augmented reality displays to indicate a critical or time sensitive step or to indicate that a particular step is at a higher risk level than the others.

In some aspects, the interactive surgical system may track the skills or capabilities of members of the surgical team in the operating room. In addition, the interactive surgical system may track the individual locations of the members of the surgical team in the operating room as well as their functions. The locations of personnel entering and exiting the operating room may also be tracked. The interactive surgical system may monitor the surgical staff motions, interactions, and movement within the operating room to improve the layout. Aspects related to the use of the intelligent surgical devices may be tracked, for example the hand dominance of a team member using such a device, or the placement on a table of the surgical device before or after use to optimize efficiency.

Figure 16:
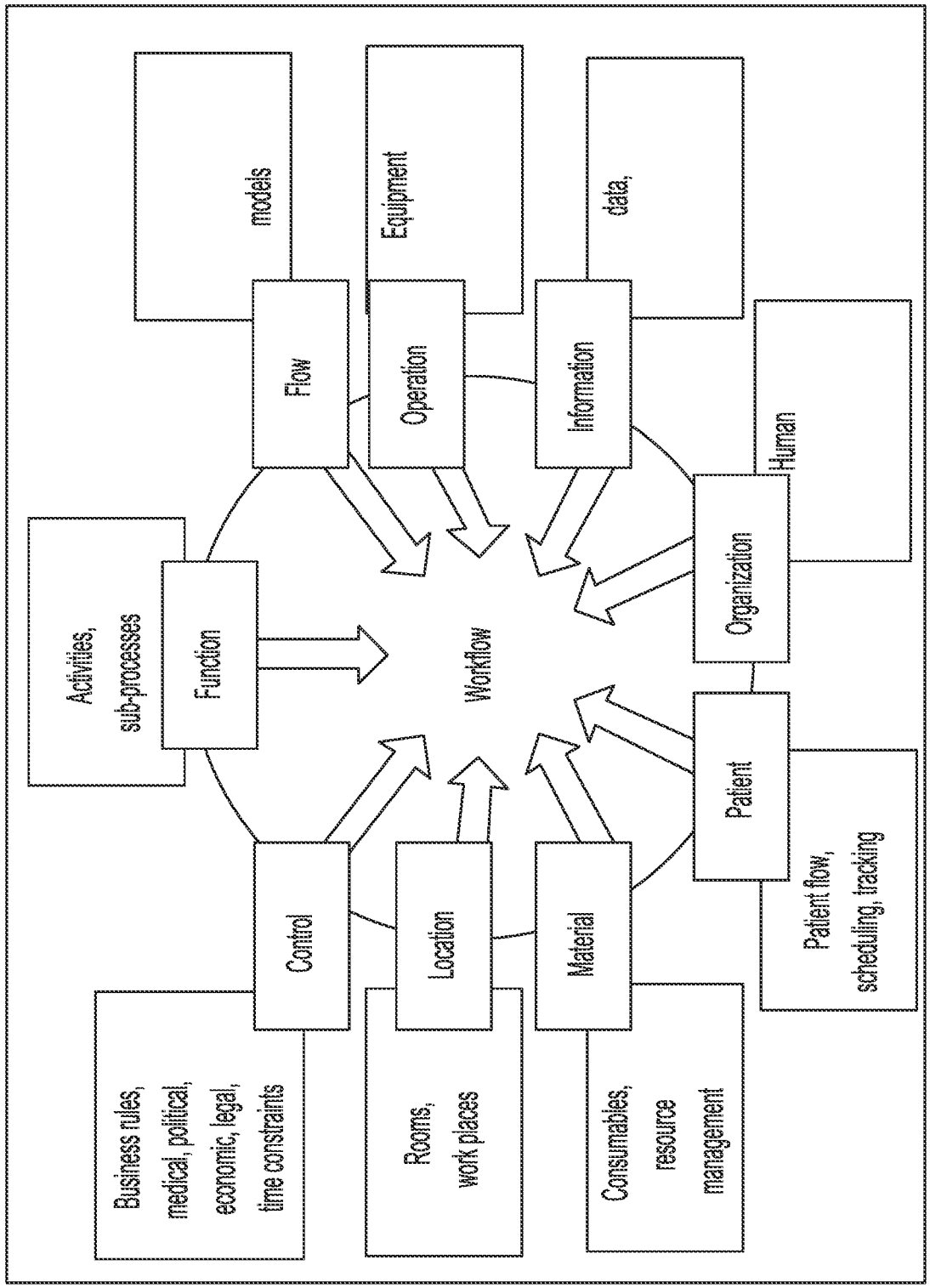
FIG. 16 illustrates the various aspects associated with a surgical procedure that may be tracked by the interactive surgical system, and which may be analyzed to develop optimization strategies, according to one aspect of this disclosure.

FIG. 16 depicts the various aspects associated with a surgical procedure that may be tracked by the interactive surgical system, and which may be analyzed to develop optimization strategies. Data related to the patient may include patient location, and pre- and post-surgical scheduling. Materiel data may include lists and location of consumable products, such as gauze and wipes, and their management in the hospital supply chain. Location related data may include not only the operating room, but ancillary rooms such as storage facilities and work locations. Control matters may include rules, regulations, and laws related to hospital business practices, medical, political, economic, and legal constraints on the practice. Functional data are all data related to the individual steps, processes, and sub-processes involved in the surgical procedure. Flow data encompass the actual sequence of procedures and processes including models. Operational data relate to the application of various pieces of surgical equipment, along with devices and tools. Informational matters include all data acquired during the procedure, documents, and data models of the procedure. Finally, organizational data may include human resources data from the hospital, including staff identification, surgical roles, and organizational models of the hospital itself.

Figure 17:
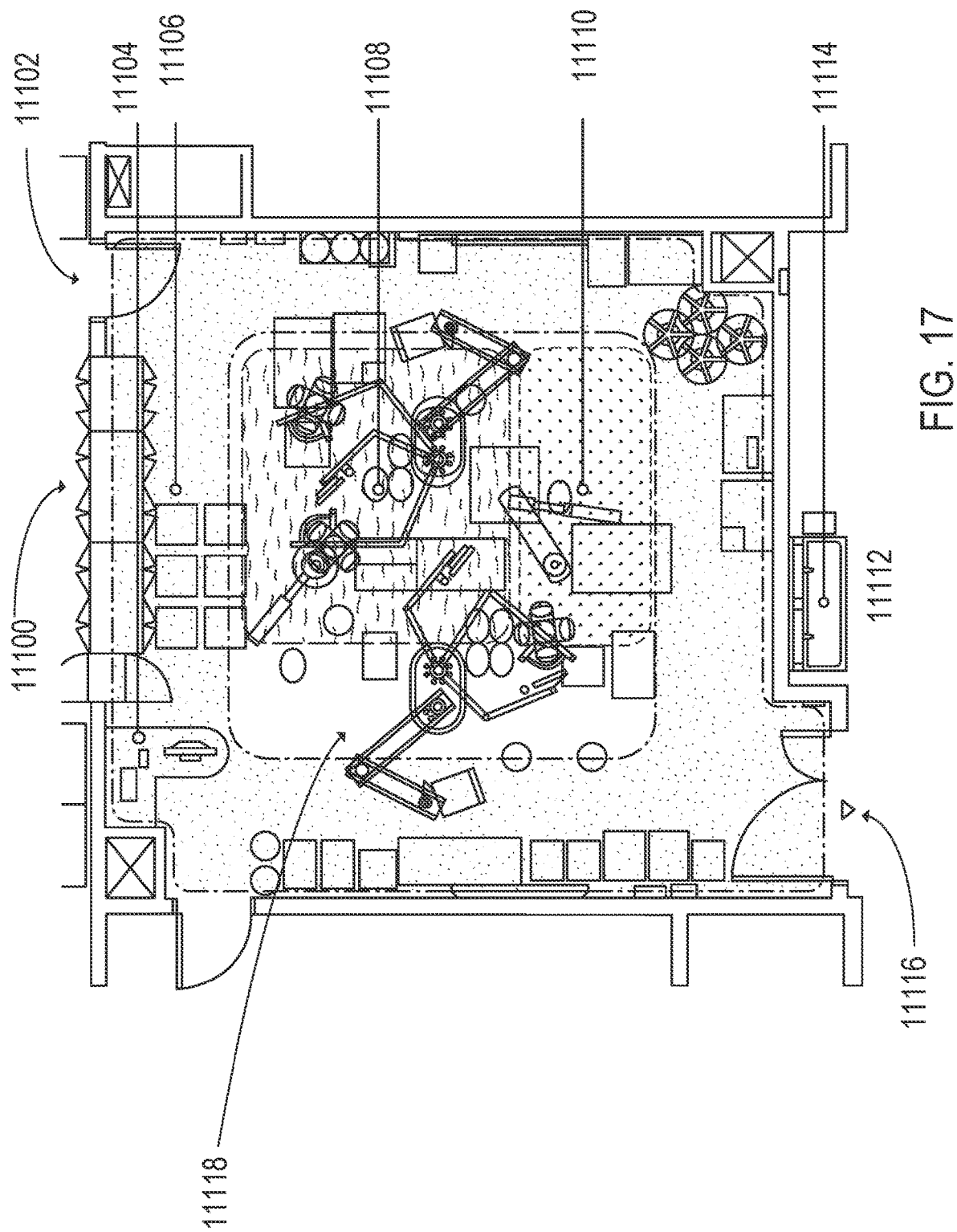
FIG. 17 illustrates aspects of an operating room which may be modeled for tracking purposes, according to one aspect of this disclosure.

FIG. 17 depicts aspects of an operating room 11100 which may be modeled for tracking purposes. The operating room 11100 depicted may merely be representative of operating rooms in general, and the layout may be adapted to any real-world example of an operating room. The operating room 11100 has an access 11102 through which the patient, surgical team members, and equipment may enter. The operation room may have an exit 11116 through which used equipment may flow for disposal or recycling. There may be a central surgical theater 11118 comprising the sterile zone 11108 for the patient and the surgeons and an anesthesia zone 11110 for the anesthesiologist and nurse anesthetist. The central surgical theater 11118 may also include the location of any surgical robots involved with the surgery. Surrounding the central surgical theater 11118 may be a circulation zone 11106 where nurses, technicians, and other personal may move so as not to disturb the surgical procedure carried out in the surgical theater 11118. A charting area 11104 where clinical notes may be taken may be accessible through the circulation zone 11106. There may be a perimeter corridor 11112 outside of the operating room 11100 which may include a scrub station 11114 for the surgical team members to wash their hands and put on their personal protective gear.

Figure 18:
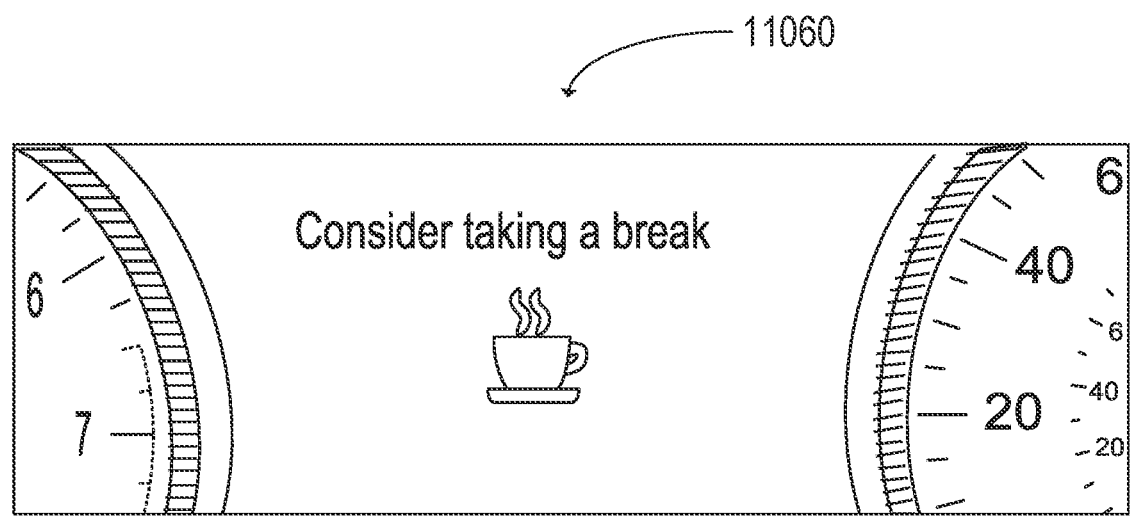
FIG. 18 illustrates an example of a virtual objection warning of surgical member fatigue, according to one aspect of this disclosure.

The interactive surgical system may track postural changes in the members of the surgical team, such as rocking back and forth while standing. Such postural activities may be an indication of an increase in the fatigue level of a member of the surgical team. In response, the interactive surgical system may display a virtual object on the augmented reality display associated with the fatiguing member of the surgical team. The interactive surgical system could alert support staff to potentially allow a break to the current staff or surgeon by displaying an appropriate virtual object on their respective augmented reality displays. In one aspect, the virtual object may be an indicator of the fatigue status of the team member. An example of such a virtual objection warning of surgical member fatigue 11060 is depicted in FIG. 18.

As part of the ability of the interactive surgical system to track multiple aspects of an operating room procedure, the interactive surgical system may include optimization algorithms to improve performance during a surgical procedure. Such optimizations may include an optimization of right surgical tool used at right time such as determining that all of the required surgical tools are available and conveniently placed before start of the procedure. The system may determine an optimize operating room layout of equipment, an optimized patient placement, or an optimize access to equipment or operating room doors.

Upon procedure completion, the interactive surgical system could analyze and propose variations to the operating room flow to minimize areas of inefficiency. This analysis can impact the procedural planning of all future comparable surgeries. This analysis can be tailored for each unique operating. Operating room size, shape, number of staff, entrance and exit placement, locations of supplies within the operating room and external materials needed to come into the operating room may all be analyzed by the interactive surgical system in view of the movements and actions of the surgical team members during the surgery and the outcome of the surgery. The interactive surgical system could run multiple scenarios virtually to determine an "optimal" workflow. Future similar procedures could use the updated flow to gain efficiency and lower fatigue. For example, improved logistics and surgical efficiency may be indicated by enabling virtual objects on the augmented reality display. Such virtual objects may include graphical overlays over images of device layout, equipment locations, and patient layout to visualize the flow and utilization of the products.

Some exemplary illustrations of optimized operating rooms are depicted in FIG. 19A, FIG. 19B, and FIG. 19C. Each illustration 11200a,b,c depicts possible organization of components of an operating room including one or more support zones 11202a,b,c, a transition zone 11204a,b,c (comparable to the circulation zone 11106 in FIG. 17), and one or more supply zones 11206a,b,c. The anesthesiology zone is illustrated at 11208a,b,c, and the surgical table 11210a,b,c is located in the central surgical theater (11118 in FIG. 17). In these depictions, the surgical table 11210a,b,c is subdivided into a right table zone, a left table zone, an a foot zone.

After surgery is complete, an overlay is projected to indicate what disposal method should be used for the various instruments and materials in the operating room. In some instances, batteries may be directed to their own waste stream. Used medical devices or disposable portions of intelligent medical devices could be directed to the medical waste disposal area. Unused material could be directed back into stock or to stay within the operating room. Packaging for the medical devices, or medical disposables may be tracked to ensure proper recycling, reuse or disposal.

Customization of the Virtual Object Data Based on Device Ownership and Task Needs In some aspects, an augmented reality display may be customized by its associated user to enable the display of a virtual object related to an intelligent surgical instrument under the user's control. The interactive surgical system may monitor a state of an intelligent surgical instrument under the control of each member of the surgical team within the operating room. The interactive surgical system may then control the display of one or more virtual objects on an augmented reality display associated with the surgical team member that is a result of both the device under control of the surgical team member and the task or situation in which the team member is acting.

The interactive surgical system could track which surgical team member is using which augmented reality display device. This could include traditional monitors, but also could include augmented reality glasses, wearables, secondary displays, displays on instruments, and capital equipment control displays. Then, using its understanding of the instruments being used by the surgical team member, the interactive surgical system could adjust the displays with virtual objects useful to the task at hand onto the display associated with the surgical team member. In one aspect, such virtual objects may be displayed on an augmented reality display of the surgical team member in control of the intelligent surgical device. Alternatively, such virtual objects may be displayed on augmented reality displays of several or all of the members of the surgical team. This could be occurring with all users in the OR and all the instruments and displays they are each using simultaneously. In some aspects, the virtual objects may appear as colored highlights surrounding the images of the surgical equipment. The highlights may appear as outlines or colored overlays displayed over the images of the surgical equipment. Other virtual objects may include auxiliary window displays containing text messages or secondary images of tissue visible in the surgical field. In some other aspects, the auxiliary window displays may include images derived from models calculated by the artificial intelligent module in the cloud system. These models may include images of tissue hidden from view in the surgical field or alternative views of the intelligent medical instruments used by the surgeon.

In some aspects, an augmented reality display may be customized by its associated user to enable the display of a virtual object related to a status of an intelligent surgical device under the control of the associated user or of another surgical team member. The status may include that the device is powered, that it is performing one of several types of functions, a power level of the device, a status of auxiliary components such as staples, error conditions, and similar functional states.

In some aspects, an augmented reality display may be customized by its associated user to enable the display of a virtual object related to an event, such as the application of another surgical device to a patient. The virtual object may display a counter or timer such as a linear counter or a circular counter. The timer may be used to time the event.

In some aspects, an augmented reality display may be customized by its associated user to enable the display of a virtual object related to status of a paired device. In one example, the virtual object may be a highlight overlaid on a stapler having a color or intensity related to the energy level of the stapler. In some examples, the highlight may be applied to the augmented reality display only when the stapler is controlled by the surgeon associated with the display device.

In some aspects, an augmented reality display may be customized by its associated user to enable the display of a virtual object related to a status of active devices. An intelligent surgical device located within the operating room may be in active communication (actively paired) with the interactive surgical system, the communication hub, the cloud system, or other equipment. The surgical device may or may not be in active use by the surgeon, but may merely be located mayo stand, ready for use. A device in active use by a surgeon may be one currently being used or held by the surgeon. A device in use by a surgeon may be a device currently performing some action with the surgeon in the surgical field.

In some aspects, a virtual object related to a status of active device may disappear from the display after a fixed time of non-use. In some aspects, a virtual object related to a status of active device may display device related information only when the device is in active use or in use.

In some aspects, an augmented reality display may be customized by its associated user based on the user inputs or request to enable the display. Depending on the technical capabilities of the augmented reality display, the input may be received from a keyboard, a mouse, a verbal command, a gesture, a tactile input on a touch sensitive screen, a stylus, or any other means of information input.

It may be understood that multiple augmented reality display devices may be used within the operating room. One or more main, wide-screen displays may be available for all of the members of the surgical team to use. Alternatively, other display types of devices may be associated by the interactive surgical system with each of the members of the surgical team. Such devices may include one or more laptop devices, tablet devices, or wearable devices such as augmented reality head-sets. A tablet display device may be different from the larger display devices within the standard OR. If the interactive surgical system determines or the user indicates they are using the tablet screen, the virtual objects displayed on the augmented reality display devices may be adjusted to adapt to the smaller screen either in display location, aspect ratio, color, or other visual design aspects. The user can determine what virtual objects are present and which ones should be excluded.

The surgical team member may interact with a portion of the augmented reality display with which they are associated to determine where a particular virtual object is displayed. In other aspects, the surgical team member may scan, photograph, or input a classifier that would designate the display of the overlay, configuration, or location. In other aspects, a surgical team member may interact with a portion of the augmented reality display via a separate device, such as a wearable device in order to identify a predetermined configurations or inputs to customize the layout of the augmented reality display associated with the user. In other aspects, an audio or visual source of a user may be coupled with the instruments in their control. In some other aspects, virtual objects that show linked or interactive displays of multiple instruments may be displayed on multiple augmented reality displays or together on a main or primary operating room display, along with a summary that is more detailed than each of the independent displays individually While an individual member of the surgical team may be able to customize the display of virtual objects on their associated augmented reality display, the displayed information for a specific surgical team member may change as intelligent surgical instruments enter or leave their control. In some aspect, the interactive surgical system tracks instrument exchanges and changes in ownership between members of the surgical team and may adjust the augmented reality displayed data based on the ownership change. Further, the interactive surgical system is capable of determining the in-situ and extracorporeal aspects of the instruments in use and the associated user in control of the instruments. The interactive surgical system can relate actions occurring outside the body with motions occurring inside the body to verify correct correlation of the two facets.

Various additional aspects of the subject matter described herein are set out in the following numbered examples:

Example 1: A method of distributing data among members of a surgical team, the method including receiving imaging data, by a modular control tower, from a plurality of imaging devices, receiving device-dependent data, by the modular control tower, from each of a plurality of intelligent surgical instruments, associating, by the modular control tower, a display device with a member of the surgical team, defining, by the modular control tower, a functional role for the member of the surgical team, and displaying, by the modular control tower, a augmented reality display by the display device, in which the augmented reality display on the display device comprises virtual objects based on the imaging data, the device-dependent data, the functional role of the member of the surgical team, and a surgical activity by the member of the surgical team.

Example 2: The method of Example 1, wherein receiving device-dependent data, by the modular control tower, includes receiving, by the modular control tower, data defining a member of the surgical team in control of the one or more of the plurality of intelligent surgical instruments.

Example 3: The method of Example 2, further including displaying, by the modular control tower on a augmented reality display associated with the member of the surgical team in control of the one or more of the plurality of intelligent surgical instruments, virtual objects associated with a controlling function by the member of the surgical team of the one or more of the plurality of intelligent surgical instruments.

Example 4: The method of Example 3, further including determining, by the modular control tower, an in situ aspect and an extracorporeal aspect of one or more of the plurality of intelligent surgical instruments controlled by the member of the surgical team, and displaying, by the modular control tower, virtual objects associated with the in situ aspect of the one or more of the plurality of intelligent surgical instruments on the display device associated with the member of the surgical team in control of the one or more of the plurality of intelligent surgical instruments.

Example 5: The method of Example 4, further including correlating, by the modular control tower, an action of the in situ aspect of the one or more of the plurality of intelligent surgical instruments with an action of the extracorporeal aspect of the one or more of the plurality of intelligent surgical instruments.

Example 6: The method of Example 3, further including changing, by the modular control tower, the virtual objects displayed on the augmented reality display associated with the member of the surgical team in control of the one or more of the plurality of intelligent surgical instruments, when the member of the surgical team relinquishes control of the one or more of the plurality of intelligent surgical instruments.

Example 7: The method of Example 6, further including changing, by the modular control tower, a augmented reality display on a display device associated with a member of the surgical team receiving control of the one or more of the plurality of intelligent surgical instruments.

Example 8: The method of Example 1, further including causing, by a first member of the surgical team, a display device associated with a second member of the surgical team to display a augmented reality display associated with the first member of the surgical team.

Example 9: The method of Example 1, further including causing, by a first member of the surgical team, a display device associated with the first member of the surgical team to display a augmented reality display associated with a second member of the surgical team.

Example 10: The method of Example 1, further including adjusting, by the member of the surgical team, the virtual objects of the augmented reality display associated with the member of the surgical team.

Example 11: The method of Example 1, further including adjusting, by the member of the surgical team, an aspect of the virtual objects displayed on the augmented reality display associated with the member of the surgical team.

Example 12: The method of Example 11 wherein adjusting an aspect of the virtual objects displayed on the augmented reality display includes adjusting a location of one or more of the virtual objects on the augmented reality display.

Example 13: An automated surgical system including a modular control tower, a plurality of imaging devices in data communication with the modular control tower, a plurality of intelligent surgical instruments, and a plurality of display devices in data communication with the modular control tower. Each of the plurality of display devices is associated, by the modular control tower, with one or more members of a surgical team, and each of the one or more members of the surgical team is defined by a functional role. The modular control tower includes a controller in data communication with one or more memory components configured to store instructions that, when executed by the controller, cause the controller to receive imaging data from the plurality of imaging devices, receive device-dependent data from a each of the plurality of intelligent surgical instruments, and display a augmented reality display on each of the plurality of display devices. The augmented reality display on a specified display device may include virtual objects based on the imaging data, the device-dependent data, the functional role of a specified member of the surgical team associated with the specified display device, and a surgical activity by the specified member of the surgical team.

Example 14: The system of Example 13, wherein the augmented reality display on each of the plurality of display devices is the same.

Example 15: The system of Example 13, wherein a augmented reality display of the specified display device is customizable by the specified member of the surgical team associated with the specified display device.

Example 16: The system of Example 13, wherein the virtual objects of the augmented reality display are dependent on a type of the one or more display devices.

Example 17: The system of Example 13, wherein the virtual objects of the augmented reality display on the specified display device are dependent on one or more intelligent surgical instruments controlled by the specified member of the surgical team.

Example 18: The system of Example 17, wherein the virtual objects of the augmented reality display change when the specified member of the surgical team relinquishes control of the one or more intelligent surgical instruments.

Example 19: The system of Example 17, wherein the virtual objects of the augmented reality display on the specified display device comprise a prediction of a second surgical activity by the specified member of the surgical team.

Example 20: The system of Example 17, wherein the virtual objects of the augmented reality display are dependent on a distance of the one or more intelligent surgical instruments from a critical anatomical structure of a patient.

Example 21: The system of Example 17, wherein the virtual objects of the augmented reality display indicate that the one or more intelligent surgical instruments controlled by the specified member of the surgical team are improperly used or incorrect for the surgical activity.

Example 22: The system of Example 17, wherein the virtual objects of the augmented reality display depict a view of the one or more intelligent surgical instruments that is not visible to the specified member of the surgical team.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of this disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method performed by a surgical system, the method comprising:
receiving imaging data from an imaging device;
receiving device-dependent data from a first intelligent surgical instrument and a second intelligent surgical instrument;
associating a display device with a member of a surgical team;
determining a functional role of the member of the surgical team;
generating a set of augmented reality (AR) virtual objects based on the imaging data, the device-dependent data, the functional role of the member of the surgical team, and a surgical activity associated with the member of the surgical team; and
sending the set of AR virtual objects for displaying on the display device associated with the member of the surgical team.

2. The method of claim 1, wherein the device-dependent data comprises an indication that the member of the surgical team is in control of the first intelligent surgical instrument, and wherein the set of AR virtual objects are associated with a controlling function by the member of the surgical team with respect to the first intelligent surgical instrument.

3. The method of claim 1, further comprising:
determining an in situ aspect and an extracorporeal aspect of the first intelligent surgical instrument, wherein the set of AR virtual objects comprise a virtual object associated with the in situ aspect of the first intelligent surgical instrument.

4. The method of claim 3, further comprising:
on a condition that the member of the surgical team relinquishes control of the first intelligent surgical instrument associated with the in situ aspect, updating the virtual object associated with the in situ aspect; and
sending the updated virtual object associated with the in situ aspect to the display device.

5. The method of claim 1, further comprising:
determining an in situ aspect and an extracorporeal aspect of the first intelligent surgical instrument, wherein the set of AR virtual objects comprises a virtual object associated with the in situ aspect of the first intelligent surgical instrument; associate an action of the in situ aspect with an action of the extracorporeal aspect; and
adjust the virtual object based on the association and a correlation between the in situ aspect and the extracorporeal aspect.

6. The method of claim 1, wherein the member of the surgical team is a first member of the surgical team, and wherein the method further comprises:
determining that control of the first intelligent surgical instrument has changed from the first member of the surgical team to a second member of the surgical team; and
updating the set of AR virtual objects based on the second member of the surgical team receiving control of the first intelligent surgical instrument.

7. The method of claim 1, wherein the member of the surgical team is a first member of the surgical team, the display device associated with the first member of the surgical team is a first display device, and the method further comprises sending, to a second display device associated with a second member of the surgical team, the set of AR virtual objects.

8. The method of claim 1, further comprising:
receiving an indication of a change in the functional role of the member of the surgical team; and
adjusting the set of AR virtual objects based on the indication.

9. The method of claim 1, wherein the set AR virtual objects are dependent on a distance between at least one of the first intelligent surgical instrument or the second intelligent surgical instrument and a critical anatomical structure of a patient.

10. The method of claim 1, wherein the member of the surgical team is a first member of the surgical team, the set of AR virtual objects is a first set of AR virtual objects, the display device is a first display device, and wherein the method further comprises:
generating a second set of AR virtual objects based on the imaging data, the device-dependent data, the functional role of a second member of the surgical team, and a surgical activity by the second member of the surgical team, wherein the first set of AR virtual objects and the second set of AR virtual objects are visually encoded to indicate an association between the first set of virtual objects and the first member of the surgical team, and an association between the second set of virtual objects and the second member of the surgical team; and sending the second set of AR virtual objects to a second display device associated with the second member of the surgical team.

11. A surgical device comprising:

a processor configured to:
receive imaging data from an imaging device;
receive device-dependent data from a first intelligent surgical instrument and a second intelligent surgical instrument;
associate a display device with a member of a surgical team;
determine a functional role of the member of the surgical team;
generate a set of augmented reality (AR) virtual objects based on the imaging data, the device-dependent data, the functional role of the member of the surgical team, and a surgical activity associated with the member of the surgical team; and
send the set of AR virtual objects for displaying on the display device associated with the member of the surgical team.

12. The surgical device of claim 11, wherein the device-dependent data comprises an indication that the member of the surgical team is in control of the first intelligent surgical instrument, and wherein the set of AR virtual objects are associated with a controlling function by the member of the surgical team with respect to the first intelligent surgical instrument.

13. The surgical device of claim 11, wherein the processor is further configured to determine an in situ aspect and an extracorporeal aspect of the first intelligent surgical instrument, wherein the set of AR virtual objects comprise a virtual object associated with the in situ aspect of the first intelligent surgical instrument.

14. The surgical device of claim 13, wherein the processor is further configured to:
on a condition that the member of the surgical team relinquishes control of the first intelligent surgical instrument associated with the in situ aspect, update the virtual object associated with the in situ aspect; and
send the updated virtual object associated with the in situ aspect to the display device.

15. The surgical device of claim 11, wherein the processor is further configured to:
determine an in situ aspect and an extracorporeal aspect of the first intelligent surgical instrument, wherein the set of AR virtual objects comprises a virtual object associated with the in situ aspect of the first intelligent surgical instrument;
associate an action of the in situ aspect with an action of the extracorporeal aspect; and
adjust the virtual object based on the association and a correlation between the in situ aspect and the extracorporeal aspect.

16. The surgical device of claim 11, wherein the member of the surgical team is a first member of the surgical team, and wherein the processor is further configured to:
determine that control of the first intelligent surgical instrument has changed from the first member of the surgical team to a second member of the surgical team; and
update the set of AR virtual objects based on the second member of the surgical team receiving control of the first intelligent surgical instrument.

17. The surgical device of claim 11, wherein the member of the surgical team is a first member of the surgical team, the display device associated with the first member of the surgical team is a first display device, and wherein the processor is further configured to send, to a second display device associated with a second member of the surgical team, the set of AR virtual objects.

18. The surgical device of claim 11, wherein the processor is further configured to:
receive an indication of a change in the functional role of the member of the surgical team; and
adjust the set of AR virtual objects based on the indication.

19. The surgical device of claim 11, wherein the set AR virtual objects are dependent on a distance between at least one of the first intelligent surgical instrument or the second intelligent surgical instrument and a critical anatomical structure of a patient.

20. The surgical device of claim 11, wherein the member of the surgical team is a first member of the surgical team, the set of AR virtual objects is a first set of AR virtual objects, the display device is a first display device, and wherein the processor is further configured to:
generate a second set of AR virtual objects based on the imaging data, the device-dependent data, the functional role of a second member of the surgical team, and a surgical activity by the second member of the surgical team, wherein the first set of AR virtual objects and the second set of AR virtual objects are visually encoded to indicate an association between the first set of virtual objects and the first member of the surgical team, and an association between the second set of virtual objects and the second member of the surgical team; and
send the second set of AR virtual objects to a second display device associated with the second member of the surgical team.

* * * * *